United States Patent
Gustavsson

(10) Patent No.: US 9,539,440 B2
(45) Date of Patent: Jan. 10, 2017

(54) FLUORESCENT HANDPIECE

(71) Applicant: Morgan Lars Ake Gustavsson, Newport Beach, CA (US)

(72) Inventor: Morgan Lars Ake Gustavsson, Newport Beach, CA (US)

(73) Assignee: Gustavsson Nevada Holding LLC, Las Vegas, NV (US)

( * ) Notice: Subject to any disclaimer, the term of this patent is extended or adjusted under 35 U.S.C. 154(b) by 0 days.

(21) Appl. No.: 14/881,009

(22) Filed: Oct. 12, 2015

(65) Prior Publication Data

US 2016/0263394 A1 Sep. 15, 2016

Related U.S. Application Data

(63) Continuation of application No. 14/216,910, filed on Mar. 17, 2014, now Pat. No. 9,155,905, which is a continuation-in-part of application No. 14/010,336, filed on Aug. 26, 2013, now Pat. No. 9,192,779, which is a continuation of application No. 13/407,619, filed on Feb. 28, 2012, now Pat. No. 8,518,093, which is a continuation-in-part of application No. 13/361,748, filed on Jan. 30, 2012, now Pat. No. 8,287,578, which is a continuation of application No. 13/153,702, filed
(Continued)

(51) Int. Cl.
*A61N 5/06* (2006.01)

(52) U.S. Cl.
CPC ....... *A61N 5/0616* (2013.01); *A61N 2005/063* (2013.01); *A61N 2005/0644* (2013.01); *A61N 2005/0667* (2013.01)

(58) Field of Classification Search
CPC .................. A61N 2005/0652; A61N 5/062
See application file for complete search history.

(56) References Cited

U.S. PATENT DOCUMENTS

| | | | |
|---|---|---|---|
| 3,426,194 A | 2/1969 | Werner | |
| 3,818,129 A | 6/1974 | Yamamoto | |

(Continued)

FOREIGN PATENT DOCUMENTS

| | | |
|---|---|---|
| DE | 103 35 303 | 2/2004 |
| EP | 0 586 353 A1 | 3/1994 |

OTHER PUBLICATIONS

Gustafsson, et al., "A Variable Pulsewidth Vascular System for Dermatology," SPIE, vol. 2128:188-196 (1994).
(Continued)

*Primary Examiner* — Gary Jackson
*Assistant Examiner* — Jeffrey Lipitz
(74) *Attorney, Agent, or Firm* — Knobbe, Martens, Olson & Bear LLP

(57) ABSTRACT

A handpiece can treat biological tissue using electromagnetic radiation, which can be substantially fluorescent light. The handpiece includes a source of electromagnetic radiation and a waveguide. The waveguide is adjacent the source, receives electromagnetic radiation from the source, and delivers the electromagnetic radiation to the biological tissue. The handpiece also includes a system for moving a fluorescent substance through the waveguide. The fluorescent substance includes a fluid base and a fluorescing agent and is capable of modulating at least one property of the electromagnetic radiation. A method is described for removing the fluorescing agent from the fluorescing substance and replacing it with a second, different fluorescing agent.

1 Claim, 19 Drawing Sheets

Related U.S. Application Data on Jun. 6, 2011, now Pat. No. 8,105,369, which is a continuation of application No. 12/014,989, filed on Jan. 16, 2008, now Pat. No. 7,955,367.

(60) Provisional application No. 61/803,067, filed on Mar. 18, 2013, provisional application No. 61/800,035, filed on Mar. 15, 2013, provisional application No. 61/447,654, filed on Feb. 28, 2011, provisional application No. 61/513,394, filed on Jul. 29, 2011.

(56) References Cited

U.S. PATENT DOCUMENTS

| | | | |
|---|---|---|---|
| 4,499,403 A | 2/1985 | Leppelmeier et al. | |
| 5,026,366 A | 6/1991 | Leckrone | |
| 5,320,618 A | 6/1994 | Gustafsson | |
| 5,620,478 A | 4/1997 | Eckhouse | |
| 5,626,631 A | 5/1997 | Eckhouse | |
| 5,720,772 A | 2/1998 | Eckhouse | |
| 5,755,751 A | 5/1998 | Eckhouse | |
| 6,231,567 B1 | 5/2001 | Rizoiu et al. | |
| 6,231,593 B1 | 5/2001 | Meserol | |
| 6,235,015 B1 | 5/2001 | Mead et al. | |
| 6,254,597 B1 | 7/2001 | Rizoiu et al. | |
| 6,280,438 B1 | 8/2001 | Eckhouse et al. | |
| 6,328,760 B1 | 12/2001 | James | |
| 6,334,074 B1 | 12/2001 | Spertell | |
| 6,343,174 B1 | 1/2002 | Neuberger | |
| 6,350,123 B1 | 2/2002 | Rizoiu et al. | |
| 6,413,268 B1 | 7/2002 | Hartman | |
| 6,443,946 B2 | 9/2002 | Clement et al. | |
| 6,514,243 B1 | 2/2003 | Eckhouse et al. | |
| 6,693,285 B1 | 2/2004 | Weiss | |
| 6,981,970 B2 | 1/2006 | Karni | |
| 7,083,610 B1 | 8/2006 | Murray et al. | |
| 7,112,194 B2 | 9/2006 | Fujieda | |
| 7,135,033 B2 | 11/2006 | Altshuler et al. | |
| 7,187,822 B2 | 3/2007 | Rizoiu et al. | |
| 7,208,007 B2 | 4/2007 | Nightingale et al. | |
| 7,955,367 B2 | 6/2011 | Gustavsson | |
| 7,998,181 B2 | 8/2011 | Nightingale et al. | |
| 8,105,369 B2 | 1/2012 | Gustavsson | |
| 8,287,578 B2 | 10/2012 | Gustavsson | |
| 8,419,781 B2 | 4/2013 | Gustavsson | |
| 8,465,532 B2 | 6/2013 | Gustavsson | |
| 8,518,093 B2 | 8/2013 | Gustavsson | |
| 8,579,951 B2 | 11/2013 | Gustavsson | |
| 2002/0067121 A1 | 6/2002 | Jean et al. | |
| 2002/0168317 A1 | 11/2002 | Daighighian et al. | |
| 2003/0032950 A1 | 2/2003 | Altshuler et al. | |
| 2003/0044114 A1 | 3/2003 | Pelka | |
| 2006/0020309 A1 | 1/2006 | Altshuler et al. | |
| 2006/0030909 A1 | 2/2006 | Karni | |
| 2006/0240381 A1 | 10/2006 | Rizoiu et al. | |
| 2006/0282137 A1 | 12/2006 | Nightingale et al. | |
| 2007/0166663 A1 | 7/2007 | Telles et al. | |
| 2008/0025672 A1 | 1/2008 | Boutoussov et al. | |
| 2008/0188914 A1 | 8/2008 | Gustavsson | |
| 2009/0036953 A1 | 2/2009 | Gustavsson | |
| 2009/0059617 A1 | 3/2009 | Gustavsson | |
| 2009/0182397 A1 | 7/2009 | Gustavsson | |

OTHER PUBLICATIONS

Aug. 30, 2012 International Search Report and Written Opinion for Application No. PCT/US2012/027035 filed on Feb. 28, 2012.

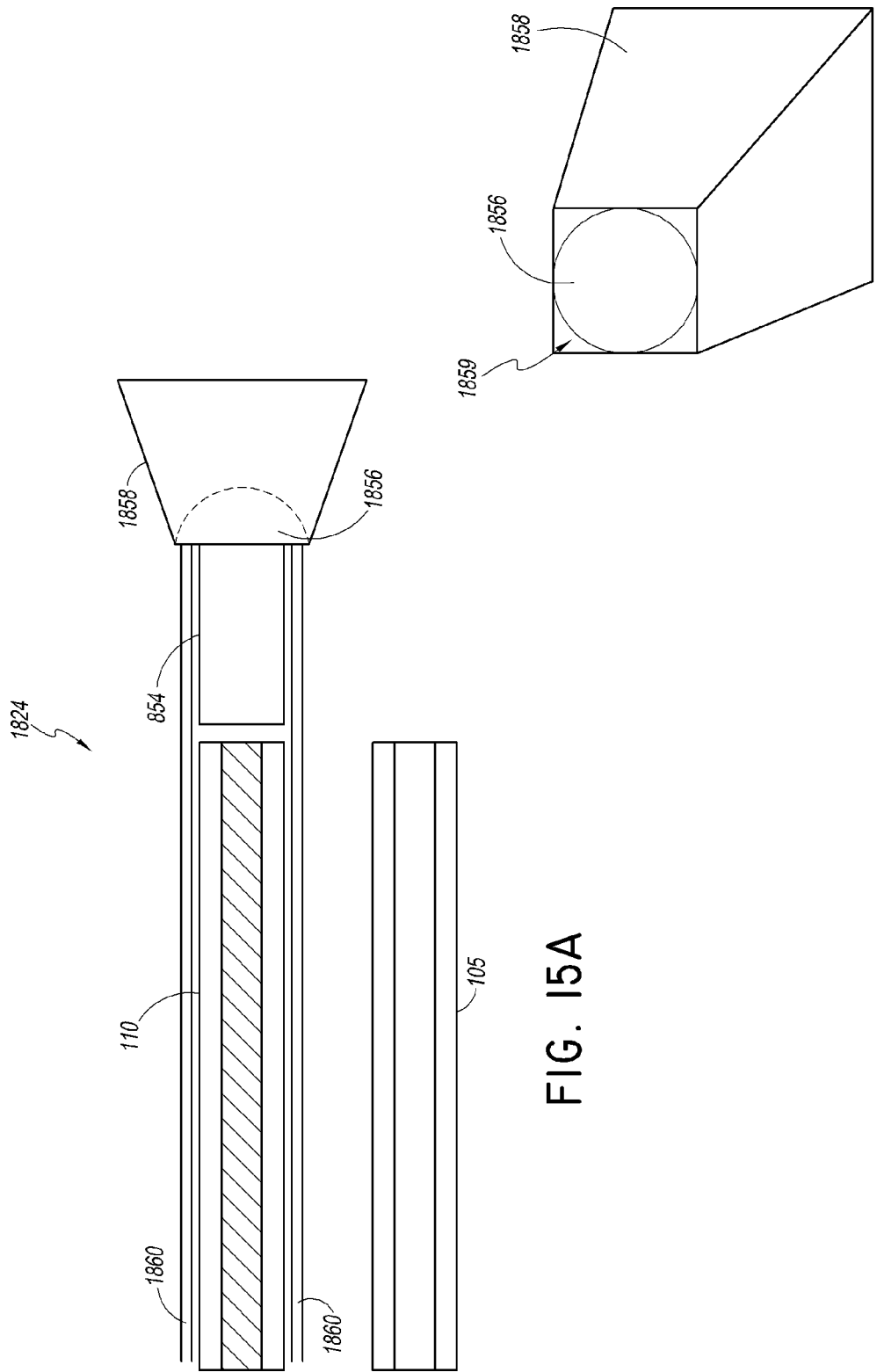

FLUORESCENT HANDPIECE

CROSS-REFERENCE TO RELATED APPLICATIONS

The present application is a continuation of U.S. application Ser. No. 14/216,910, filed Mar. 17, 2014, which claims priority benefit under 35 U.S.C. §119(e) from U.S. Provisional No. 61/800,035, filed Mar. 15, 2013, and U.S. Provisional No. 61/803,067, filed Mar. 18, 2013, each of which is expressly incorporated by reference in its entirety. U.S. application Ser. No. 14/216,910, filed Mar. 17, 2014 is also a continuation-in-part of U.S. application Ser. No. 14/010,336, filed Aug. 26, 2013, which is a continuation of U.S. application Ser. No. 13/407,619, filed Feb. 28, 2012, now U.S. Pat. No. 8,518,093, which is continuation-in-part of U.S. application Ser. No. 13/361,748, filed Jan. 30, 2012, now U.S. Pat. No. 8,287,578, which is a continuation of U.S. application Ser. No. 13/153,702, filed Jun. 6, 2011, now U.S. Pat. No. 8,105,369, which is a continuation of U.S. application Ser. No. 12/014,989, filed Jan. 16, 2008, now U.S. Pat. No. 7,955,367, all of which are expressly incorporated by reference in their entireties. U.S. application Ser. No. 13/407,619, filed Feb. 28, 2012, also claims priority benefit under 35 U.S.C. §119(e) from U.S. Provisional Application No. 61/447,654, filed Feb. 28, 2011, and U.S. Provisional No. 61/513,394, filed Jul. 29, 2011, both of which are expressly incorporated by reference in their entireties.

BACKGROUND

Field

The invention relates generally to apparatuses and methods for treating biological tissue using electromagnetic radiation. In particular, the invention relates to a fluorescent handpiece for treating biological tissue.

Description of the Related Art

Certain treatments for cosmetic and dermatologic conditions include the use of non-coherent fluorescent light or intense pulsed light. For example, devices can include a fluorescent substance or dye for transforming a first predetermined wavelength band of light to a second predetermined pulsed wavelength band of light, a first light source for producing light including said first predetermined wavelength band, and a waveguide for directing said second predetermined pulsed wavelength band to a predetermined location. Unfortunately, the efficacy of the dye can suffer from quenching, bleaching, and other chemical reactions. Also, because the fluorescent substance or dye is heated during operation, and because heating can limit the useful lifetime of the dye, such devices can address the heating of the fluorescent substance or dye. For example, the dye can be circulated through a separate base unit, to mitigate quenching, bleaching, and other chemical reactions, or to cool the dye in an attempt to extend its useful lifetime. However, the volume of circulating dye can be large and the system required to store, pump, and circulate the dye can be large. Due to the volume of dye and the size of the system, these components are generally in a base unit separate from the treatment handpiece. The fluorescent substance or dye can be stationary in a handpiece (e.g., not circulated, not pumped, etc.). The stationary fluorescent substance can be permanent (e.g., in a sealed chamber). The stationary fluorescent substance can be exchangeable (e.g., removable and replaced with another fluorescent substance). The stationary fluorescent substance can be a disposable. The stationary fluorescent substance can be a solid, a gel or a liquid, or combinations thereof. The stationary fluorescent substance can be cooled or heated. Such cooling or heating can be a stationary cooling or heating element and/or a moving cooling or heating substance. In the case of a solid fluorescent substance, it can incorporate also the waveguide such that no further waveguide is needed.

SUMMARY

The invention, in various embodiments, relates to apparatuses and methods for treating matter, for example, biological tissue using electromagnetic radiation. The biological tissue can be human skin, which can exhibit at least one of superficial vascular lesion, port wine stain, telangiectasia, spider angioma, cherry angioma, rosacea, "diffusive red," poikiloderma, post-operative bruising, venous lakes small vessel diameter lesion, arterial lesion, capillary lesion, venous lesion, pigmented lesions (e.g., benign epidermal pigmented lesions, benign pigmented dermal lesions, Becker's nevus or acquired nevus of Hori), tattoos and other dermatological indications such as acne, psoriasis, vitiligo, and the like. The invention can also be used to treat wrinkles, for skin rejuvenation, for fat removal, for cellulite, for body sculpting, for decreasing circumference of a particular body part, for hair removal, and for hair regrowth. The devices and methods described herein can also be used for other scientific, industrial, or other non-therapeutic purposes.

Apparatuses can include fluorescent handpieces that include a source of electromagnetic radiation, a nonlinear waveguide, and a system for circulating or passing a fluorescent substance through the nonlinear waveguide. Advantages of the invention can include an apparatus that can be smaller, less expensive, easier to handle, easier to store, more efficient, more specific in tissue targeting, and more robust than prior art sources of electromagnetic radiation. The apparatus can also produce electromagnetic radiation of at least partially enhanced or different parameters compared to previously known apparatuses. Other advantages of the invention can include extending the usable lifetime of the fluorescent substance by at least one of mitigating quenching of the fluorescent substance, mitigating bleaching of the fluorescent substance, mitigating heating of the fluorescent substance, heating the fluorescent substance, and mitigating chemical reaction of the fluorescent substance. Additionally, the devices described herein utilize fluorescent light rather than laser light. The fluorescent substance can advantageously be non-toxic, allowing for easier and safer handling compared to laser dyes, which can be significantly toxic. The devices described herein also reduce risks to eye safety as compared to laser systems and intense pulsed light sources.

In one aspect, the invention features a handpiece for treating biological tissue. The handpiece includes a source of electromagnetic radiation, a nonlinear waveguide and a system for circulating a fluorescent substance through the nonlinear waveguide. The nonlinear waveguide is adjacent the source, receives electromagnetic radiation from the source, and delivers modulated electromagnetic radiation to the biological tissue. The fluorescent substance is capable of modulating at least one property of the electromagnetic radiation.

In one aspect, the invention features a handpiece for treating biological tissue. The handpiece is configured to receive electromagnetic radiation from at least one remote associated source of electromagnetic radiation, e.g. a crystal laser, a gas laser or a laser diode, via a delivery system for delivering the electromagnetic radiation to the handpiece. Such a delivery system can be, e.g., a light guide such as an optical fiber or an optical fiber bundle or a waveguide, for example, a nonlinear waveguide, a liquid or partially liquid waveguide, hollow waveguide, etc. The handpiece is configured to receive electromagnetic radiation from the at least one remote associated source of electromagnetic radiation and a system for circulating a fluorescent substance through the nonlinear waveguide. The fluorescent substance is capable of modulating at least one property of the electromagnetic radiation.

In another aspect, the invention features an apparatus for treating biological tissue. The apparatus includes a base unit, an energy source associated with the base unit, and an umbilicus. The umbilicus has a first end associated with the base unit and a conduit for transmitting energy from the energy source to a second end of the umbilicus. The apparatus also includes a handpiece associated with the second end of the umbilicus. The handpiece includes a source of electromagnetic radiation, a nonlinear waveguide, and a system for circulating or passing a fluorescent substance through the nonlinear waveguide. The source is adapted for receiving energy from the energy source through the conduit. The nonlinear waveguide is adjacent the source, receives electromagnetic radiation from the source, and delivers modulated electromagnetic radiation to the biological tissue. The fluorescent substance is capable of modulating at least one property of the electromagnetic radiation.

In still another aspect, the invention features a method of treating biological tissue. The method includes (i) providing electromagnetic radiation to a nonlinear waveguide associated with a handpiece; (ii) circulating or passing a fluorescent substance through the nonlinear waveguide to modulate at least one property of the electromagnetic radiation; and (iii) delivering the modulated electromagnetic radiation to treat the biological tissue.

In other examples, any of the aspects above, or any apparatus or method described herein, can include one or more of the following features.

In various embodiments, the source can be selected from the group consisting of a flash lamp, a xenon flashlamp, a krypton flash lamp, a xenon-krypton flash lamp, an arc lamp, a diode, a diode laser, laser, and an incoherent light source. In one embodiment, the handpiece includes a coating associated with the nonlinear waveguide for enhancing emission of the electromagnetic radiation from the handpiece.

In some embodiments, the handpiece includes a pump within the system for circulating or passing the fluorescent substance through the nonlinear waveguide. In one embodiment, the handpiece includes a system for cooling the fluorescent substance. The handpiece can include a port adjacent the system, the port in fluid communication with the system and adapted for receiving the fluorescent substance. The handpiece can include a port that is adapted for receiving the fluorescent substance from a reservoir cartridge, the reservoir cartridge detachably connectable with the port.

In certain embodiments, the handpiece includes a reflector adjacent a distal end of the nonlinear waveguide, the reflector for reflecting light to a proximal end of the nonlinear waveguide for delivery to the biological tissue. In one embodiment, the modulated electromagnetic radiation delivered to the biological tissue is substantially fluorescent light. The system can extend the usable lifetime of the fluorescent substance by at least one of mitigating aggregation of the fluorescent substance, mitigating quenching of the fluorescent substance, mitigating bleaching of the fluorescent substance, mitigating heating of the fluorescent substance, and mitigating chemical reaction of the fluorescent substance.

In various embodiments, the handpiece includes a connector adjacent a first portion of the handpiece, for connecting the handpiece to an umbilicus and for receiving energy from a conduit in the umbilicus, the energy for driving the source of electromagnetic radiation. In one embodiment, the connector is adapted to receive a fluorescent substance from the umbilicus and is in fluid communication with the system for circulating or passing the fluorescent substance through the nonlinear waveguide.

In some embodiments, the electromagnetic radiation delivered to the biological tissue can be characterized by a pulse width between about 0.5 ms and about 500 s. In some embodiments, the electromagnetic radiation delivered to the biological tissue can be characterized by a tissue exposure time in the range of about 500 ms to about 60 minutes. In one embodiment, the electromagnetic radiation delivered to the biological tissue is absorbed preferentially by hemoglobin in blood over adjacent skin tissue. A spectrum characterizing the electromagnetic radiation delivered to the biological tissue can be matched to an absorption spectrum of at least one of whole blood, hemoglobin, reduced hemoglobin, and oxidized hemoglobin. The electromagnetic radiation delivered to the biological tissue can be characterized by a spot size of about 2 mm or greater in diameter.

In certain embodiments, modulating at least one property of the electromagnetic radiation can include varying at least one of a wavelength, fluence, pulse or pulse train width (e.g., duration), pulse or pulse train shape, and exposure time of the tissue associated with the electromagnetic radiation. In one embodiment, the electromagnetic radiation delivered to the biological tissue is characterized by an energy density between about 0.1 $J/cm^2$ and about 500 $J/cm^2$.

In various embodiments, the handpiece includes a skin contacting portion adjacent the waveguide (e.g., a nonlinear waveguide, etc.) for contacting the biological tissue and delivering the electromagnetic radiation to the biological tissue. In one embodiment, the handpiece includes a controller for tuning at least one of a pulse width characterizing the electromagnetic radiation delivered to the biological tissue and a fluence.

In some embodiments, the apparatus includes a port associated with the handpiece and a cartridge containing the fluorescent substance detachably connectable to the port, the cartridge providing the fluorescent substance to the system. In one embodiment, the apparatus includes a reservoir for the fluorescent substance, the reservoir associated with the base unit and in fluid communication with the system, through the umbilicus, for providing the fluorescent substance to the system. The handpiece can be detachable from the umbilicus. The base unit can be detachable from the umbilicus.

In certain embodiments, the method includes treating skin having at least one of a superficial vascular lesion, port wine stain, telangiectasia, spider angioma, cherry angioma, rosacea, "diffuse red," poikiloderma, post-operative bruising, venous lakes, small vessel diameter lesion, arterial lesion, capillary lesion, venous lesion, pigmented lesion (e.g., benign epidermal pigmented lesions, benign pigmented dermal lesions, Becker's nevus or acquired nevus of Hori), tattoo, acne, psoriasis, wrinkles, cellulite, and vitiligo, or the like. The method can also or alternatively include treating skin for skin rejuvenation, fat removal, body sculpting, decreasing circumference of a body part, hair removal, or hair regrowth. In one embodiment, the method includes delivering the electromagnetic radiation to the biological tissue in a train of pulses to gradually heat a region of the biological tissue to be treated. In another embodiment, the method includes delivering the electromagnetic radiation to the biological tissue in a train of pulses to first heat a region of the biological tissue to be treated to a predetermined temperature and second to maintain the region of the biological tissue to be treated at about the predetermined temperature. The electromagnetic radiation can have varying pulse train widths and/or shapes. Modulating at least one property of the electromagnetic radiation can include varying at least one of a light direction, wavelength, and fluence.

In some embodiments, a light-emitting, therapeutic system configured to treat biological tissue comprises a source of electromagnetic radiation and a waveguide (e.g., a non-linear waveguide, etc.) positioned to receive electromagnetic radiation from the source. The waveguide comprises first and second ends, and a wall extending therebetween, the wall configured to at least partially transmit the electromagnetic radiation therethrough, the wall defining a passage extending along a direction between said first and second ends, a fluorescent substance flowable within the passage, the fluorescent substance comprising a liquid base and a fluorescing agent, and an first port and an second port in fluid communication with the passage. The system further comprises an optical output element near one of the first and second ends of the waveguide. The fluorescent substance is configured to absorb at least a portion of the electromagnetic radiation from the source through the wall and generate fluorescent light in response to the electromagnetic radiation. The waveguide is configured to guide the fluorescent light emitted by the fluorescent substance towards the optical output element by internally reflecting at least a portion of the fluorescent light, and the optical output element is configured to direct at least a portion of the fluorescent light towards biological tissue. The system also comprises a fluid conduit in fluid communication with the first and second ports and configured to carry the fluorescent substance between the waveguide's passage and a fluid moving system, the fluid moving system adapted to move the fluorescent substance from the first end to the second end through the passage and from the second end back to the first end through the fluid conduit, and a fluorescing agent removal device configured to be coupled to the fluid conduit and to remove the fluorescing agent from the fluorescent substance, the fluid conduit being configured to direct the fluorescent substance through the fluorescing agent removal device during a first mode of operation and to bypass the fluorescing agent removal device during a second mode of operation.

In some embodiments, the source is selected from the group consisting of a flash lamp, a xenon flash lamp, a krypton flash lamp, a xenon-krypton flash lamp, an arc lamp, a laser, a diode, and an incoherent light source. In some embodiments, the system further comprises a cooling system for cooling the fluorescent substance. In some embodiments, the system further comprises a fluid input port in fluid communication with the fluid conduit and adapted to detachably connect to a reservoir cartridge, the reservoir cartridge configured to supply the fluorescent substance. In some embodiments, the system further comprises a reflector near the end opposite the optical output element end of the waveguide, the reflector configured to reflect the fluorescent light towards the optical output element end of the waveguide for delivery to the biological tissue via the optical output element. In some embodiments, the system further comprises a reflector extending around and spaced apart from the outside surface of the waveguide, the reflector configured to reflect the fluorescent light towards the wall of the waveguide. In some embodiments, the system further comprises a base unit, an umbilicus connectable to the base unit, and a handpiece connectable to the umbilicus, wherein the source, waveguide, and optical output element are located within the handpiece In some embodiments, the system further comprises a base unit, an umbilicus connectable to the base unit, and a handpiece connectable to the umbilicus, wherein the source is located within the base unit and the waveguide and optical output element are located within the handpiece, the umbilicus comprising an optical conduit configured to transmit optical energy from the source to the waveguide.

In some embodiments, the fluorescent light delivered to the biological tissue is characterized by a pulse width between about 0.2 ms and about 500 s. In some embodiments, a spectrum characterizing the fluorescent light delivered to the biological tissue is matched to an absorption spectrum of at least one of whole blood, hemoglobin, reduced hemoglobin, or oxidized hemoglobin. In some embodiments, the fluorescent light delivered to the biological tissue is characterized by a spot size of about 2 mm or greater in diameter. In some embodiments, the fluorescent light delivered to the biological tissue is characterized by an energy density between about 0.1 $J/cm^2$ and about 500 $J/cm^2$. In some embodiments, a spectrum characterizing the fluorescent light delivered to the biological tissue is matched to an absorption spectrum of at least one of melanin, porphyrin, exogenous pigment, fat, and water in the biological tissue.

In some embodiments, the system further comprises a controller for tuning one or more of a pulse width and fluence characterizing the fluorescent light delivered to the biological tissue. In some embodiments, the system further comprises a cooling fluid flow path at least part of which is configured to circulate cooling fluid between the waveguide and the source of electromagnetic radiation. In some embodiments, the fluorescing agent removal device comprises a filter. The filter can comprise a deionization filter, a polarity filter, or a particle filter. In some embodiments, the fluorescent substance further comprises an additive. The additive can be selected from a group consisting of one or more of the following: a solubility enhancing agent, a passive absorber, a fluorescent dye lifetime enhancing agent, a detergent, or a substance configured to change the polarity of the fluorescent substance. The additive can be configured to change a property of the fluorescent substance, wherein the property is selected from a group consisting of one or more of the following: absorption wavelength bandwidth, absorption wavelength bandwidth position in the electromagnetic spectrum, emission wavelength bandwidth position in the electromagnetic spectrum, emission wavelength bandwidth, absorption peak wavelength, emission peak wavelength, absorption efficacy, emission efficacy, Stokes shift, fluorescent dye lifetime, proticity, whether solution is more or less protic or aprotic, whether solution will let go of hydrogen bound to primarily oxygen in a solution, or polarity of fluorescent substance.

In some embodiments, the fluorescing agent removal device is further configured to remove the additive from the fluorescent substance. In some embodiments, the liquid base comprises one or more of: water, a solvent, an organic solvent, an alcohol, methanol, and ethanol. In some embodiments, the system further comprises a dye source in fluid communication with the fluid conduit, the dye source configured to contain at least a portion of the fluorescent substance. The dye source can be selected from the group consisting of one or more of the following: a dye reservoir, a pellet, a tablet, a dye cartridge, a wet dye cartridge, a dry dye cartridge, a solution, a powder, a dye liquid, a receptacle, an ion exchange filter, an ion release filter, and a carbon filter.

In some embodiments, the system further comprises the fluid moving system, a base unit, an umbilicus connectable to the base unit, and a handpiece connectable to the umbilicus, wherein the fluid moving system is located within the handpiece. In some embodiments, the system further comprises the fluid moving system, a base unit, an umbilicus connectable to the base unit, and a handpiece connectable to the umbilicus, wherein the fluid moving system is located within the base unit. In some embodiments, the system further comprises the fluid moving system, wherein the fluid moving system is configured to pump the fluorescent substance through the waveguide in a first mode from the first port to the second port and in a second mode from the second port to the first port. The fluid moving system can be configured to reverse the flow of the fluorescent substance through the fluid conduit in response to a fluid flow control signal. The fluid moving system can comprise a fluid circulation system configured to circulate the fluorescent substance through the waveguide.

In some embodiments, the fluorescing agent comprises a single dye and the fluorescent light comprises a single emission peak. In some embodiments, the fluorescing agent comprises two or more dyes and the fluorescent light comprises two or more emission peaks. At least two of the emission peaks can at least partially overlap. At least one emission peak can overlap at least one other absorption peak.

In some embodiments, the system further comprises a cooling system in fluid communication with the fluid conduit and configured to cool the fluorescent substance. The system can further comprise a handpiece, wherein the cooling system is located within the handpiece. The system can further comprise a base unit, wherein the cooling system is located within the base unit. The system can further comprise a cooling system that is located partly in the handpiece and partly in the base unit. The cooling system can be selected from the group consisting of one or more of: a thermoelectric cooler, a heat exchange, and a fan.

In some embodiments, the optical output element is selected from the group consisting of one or more of the following: a spacer, a positive tapered waveguide, a negative tapered waveguide, a waveguide having different surface areas at its proximal and distal ends, a waveguide having different shapes at its proximal and distal ends, a bifurcated waveguide, a multi-furcated waveguide, a fiber bundle, a fiber bundle having a larger surface area at its output end than at its input end, a plurality of apertures, an aperture, a solid light guide, a liquid light guide, a hollow light guide, and a fiber. In some embodiments, the system further comprises a solid rod located within the waveguide, the sold rod configured to generate fluorescent light in response to the electromagnetic energy In some embodiments, a method of generating fluorescent light for scientific or industrial use comprises providing a light-emitting system adapted to generate fluorescent light for scientific or industrial use. The light-emitting system can comprise a waveguide positioned to receive electromagnetic energy from an electromagnetic energy source. The waveguide can comprise first and second ends, and a wall extending at least partially therebetween, the wall configured to transmit the electromagnetic radiation therethrough and defining a passage extending along a direction between said first and second ends, a fluorescent substance flowable within the passage, the fluorescent substance configured to absorb the electromagnetic radiation and generate fluorescent light in response to the electromagnetic radiation, the fluorescent substance comprising a liquid base and a fluorescing agent, and an input port and an output port in fluid communication with the passage. The light-emitting system can further comprise an optical output element near one of the first and second ends of the waveguide, and a fluid conduit in fluid communication with the input and output ports.

The method can further comprise circulating the fluorescent substance from the first end to the second end through the passage and from the second end back to the first end through the fluid conduit, transmitting electromagnetic radiation through the wall of the waveguide to the fluorescent substance within the passage, guiding at least some of the fluorescent light emitted by the fluorescent substance in response to the electromagnetic radiation through the waveguide towards the optical output element, removing the fluorescing agent from the fluorescent substance by directing the fluorescent substance through a fluorescing agent removal device, and providing an additional quantity of the same fluorescing agent to the liquid base.

In some embodiments, the fluorescing agent removal device comprises a deionization filter. In some embodiments, providing an additional quantity of the fluorescing agent comprises adding a tablet, pellet, powder, or solution of dye to the liquid base. The liquid base can comprise water. In some embodiments, providing comprises manually adding the fluorescing agent to the liquid base. In some embodiments, the method can further comprise sensing a depletion of the fluorescing agent and activating an indicator in response to said sensing. In some embodiments, the method can further comprise sensing a depletion of the fluorescing agent and automatically adding additional fluorescing agent in response to said sensing.

In some embodiments, a method of generating fluorescent light for scientific or industrial use comprises providing a light-emitting system adapted to generate fluorescent light for scientific or industrial use. The light-emitting system can comprise a waveguide positioned to receive electromagnetic energy from an electromagnetic energy source. The waveguide can comprise first and second ends, and a wall extending at least partially therebetween, the wall configured to transmit the electromagnetic radiation therethrough and defining a passage extending along a direction between said first and second ends, a fluorescent substance flowable within the passage, the fluorescent substance configured to absorb the electromagnetic radiation and generate fluorescent light in response to the electromagnetic radiation, the fluorescent substance comprising a liquid base and a first fluorescing agent, and an input port and an output port in fluid communication with the passage. The light-emitting system can further comprise an optical output element near one of the first and second ends of the waveguide and a fluid conduit in fluid communication with the input and output ports.

The method can further comprise moving the fluorescent substance from the first end to the second end through the passage and from the second end back to the first end through the fluid conduit, transmitting electromagnetic radiation through the wall of the waveguide to the fluorescent substance within the passage, guiding at least some of the fluorescent light emitted by the fluorescent substance in response to the electromagnetic radiation through the waveguide towards the optical output element, the fluorescent light having a first peak wavelength, removing the fluorescing agent from the fluorescent substance by directing the fluorescent substance through a fluorescing agent removal device, and providing a second fluorescing agent to the liquid base after said removing, the second fluorescing agent being different than the first fluorescing agent.

In some embodiments, the second fluorescing agent is configured to generate light having a second peak wavelength that is different from said first peak wavelength. In some embodiments, removing comprises directing the fluorescent substance through a deionization filter. In some embodiments, removing comprises directing the fluorescent substance through a polarity filter. In some embodiments, providing an additional quantity of the fluorescing agent comprises adding a tablet, pellet, powder, or solution of dye to the liquid base. The liquid base can comprise water. In some embodiments, providing comprises manually adding the fluorescing agent to the liquid base.

In some embodiments, the method further comprises sensing a depletion of the fluorescing agent and activating an indicator in response to said sensing. In some embodiments, the method further comprises receiving an input to change the wavelength of the fluorescent light and performing said removing and providing a second fluorescing agent in response to said input.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 15A illustrates an output optic including a ball lens optically coupled to hollow output waveguide.

FIG. 15B illustrates the ball lens and hollow output waveguide of FIG. 15A.

DETAILED DESCRIPTION OF THE PREFERRED EMBODIMENT

Figure 1:
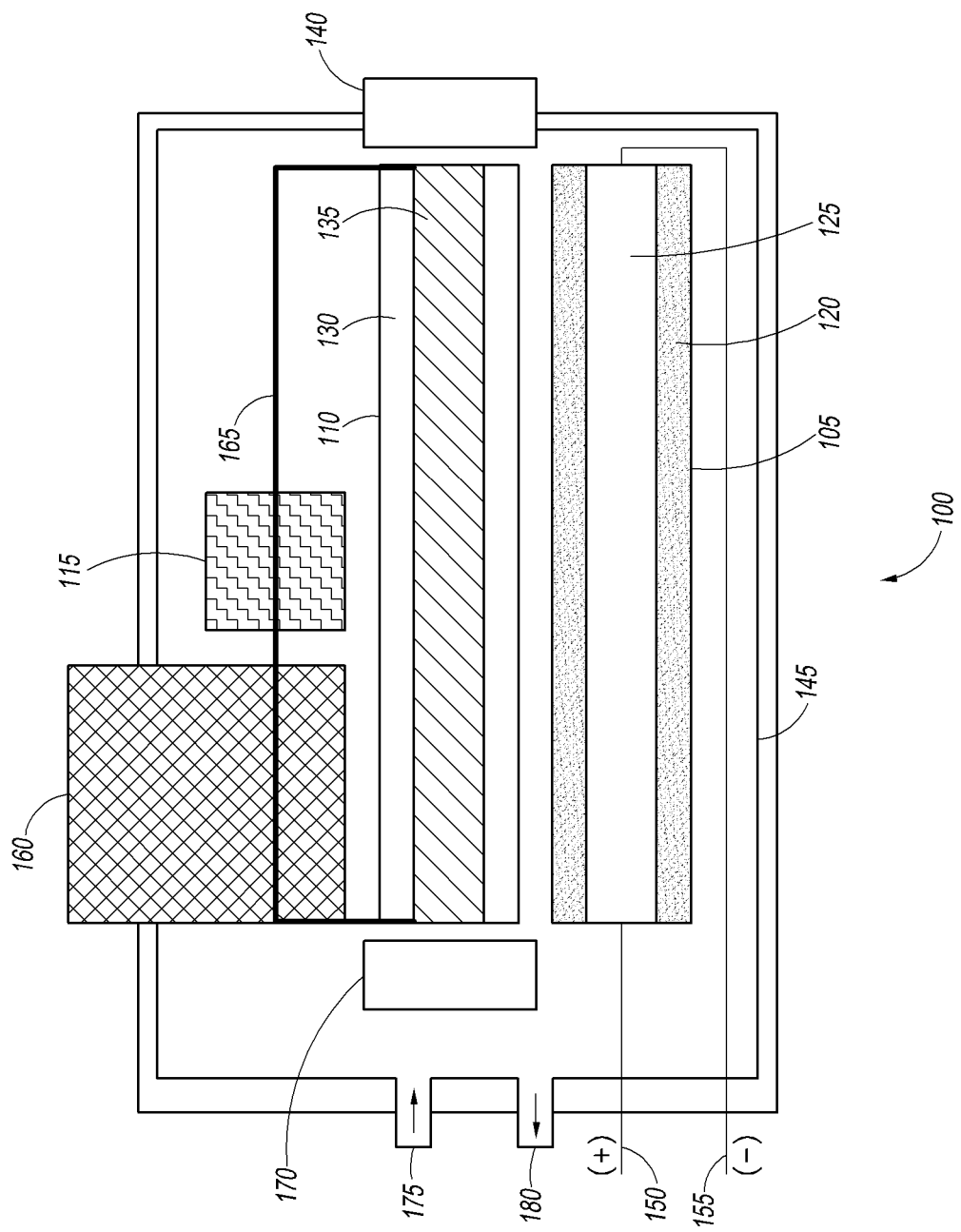
FIG. 1 illustrates various aspects of a fluorescent handpiece.

FIG. 1 illustrates various aspects of a fluorescent handpiece 100 for treating biological tissue using electromagnetic radiation. The handpiece 100 includes a source 105 of electromagnetic radiation and a nonlinear waveguide 110 adjacent the source 105. The source 105 can include a cover 120 and can have a gas in its interior 125. The source 105 can have positive 150 and negative 155 terminals, for establishing a circuit to deliver energy to drive the source 105. The waveguide 110 can include a pipe or flexible tube 130 and a passage 135 for a fluorescent substance. In some embodiments, the waveguide 110 can be considered a dye cell, for example, a fluid filled dye cell. The handpiece 100 can include a for circulating a fluorescent substance through the waveguide 110. The handpiece 100 can also include a conduit 165 that establishes fluid communication between the waveguide 110, the system 115, and a reservoir 160. Further, the handpiece 100 can include a skin contacting portion 140 adjacent the waveguide 110 and a reflector 170 adjacent a distal end of the waveguide 110. Furthermore, the handpiece 100 can include at least one cooling system 145 in thermal communication with at least one of the source 105, the waveguide 110, and the system 115. In the illustrated embodiment, the cooling system 145 includes an intake 175 and an exhaust 180, for receiving and removing coolant.

In various embodiments, the source 105 can be a flash lamp, a xenon flashlamp, a krypton flash lamp, a xenon-krypton flash lamp, an arc lamp, a diode, and an incoherent light source. The handpiece 100, in various embodiments, can include one, two, three, or more sources. In some embodiments, pulses or pulse trains from the source 105 can be repeated at a frequency of about 0.2 to about 10 Hz. In some embodiments having more than one source 105, the sources can pulse simultaneously with single pulses or pulse trains or sequentially with overlapping, partially overlapping, or non-overlapping pulses. The waveguide 110 receives electromagnetic radiation from the source 105 and delivers electromagnetic radiation to the biological tissue (not shown). The waveguide 110 can include at least one of a glass, crystal, plastic, borosilicate, silicate, sapphire, poly methyl methacrylate (PMMA), PTFE, or any other suitable transparent material. The waveguide 110 can include a partial or complete coating or coatings for enhancing emission of the electromagnetic radiation. For example, the coating can be at least one of a metal, silica, silica-titania, tantala, organic material, PTFE, and a short pass optical coating. In one embodiment, the waveguide 110 is a single tube waveguide adapted for containing a fluorescent substance. In other embodiments, a waveguide can be a co-axial waveguide adapted for separately containing two or more fluorescent substances.

The waveguide 110 can be adapted to deliver electromagnetic radiation directly to the biological tissue, or can be adapted to deliver electromagnetic radiation to the biological tissue through a skin contacting portion 140 adjacent the waveguide 110. The skin contacting portion 140 can include a glass, a crystal, silica, sapphire, or plastic. The electromagnetic radiation delivered to the biological tissue can be substantially fluorescent light. In various embodiments, the handpiece 100 includes a reflector 170 adjacent a distal end of the waveguide 110. The reflector 170 is adapted for reflecting light to a proximal end of the nonlinear waveguide for delivery to the biological tissue. In one embodiment, the reflector 170 is a mirror. In another embodiment, the reflector 170 is a diffusive white or off-white (e.g., does not substantially absorb electromagnetic radiation) surface. The reflector 170 can wrap around the waveguide 110 and/or the source 105, to increase the amount of electromagnetic radiation delivered to the waveguide 110. The reflector 170 can be an ellipsis, a waveguide and source close coupling cavity, or other geometrical shape selected to focus and/or deliver electromagnetic radiation from the source 105 to the waveguide 110.

In some embodiments, the waveguide 110 can be made of or coated with a material selected to have a refractive index lower than, higher than, or equal to a refractive index of the fluorescent substance. If the difference between the refractive indices of the waveguide 110 and the fluorescent substance is large, light is bent more (the angle of the light is changed to a greater extent) as it enters the waveguide 110 wall and returns to the fluorescent substance from the waveguide 110 wall than if the difference between the refractive indices of the waveguide 110 and the fluorescent substance is smaller. A greater degree of refraction or change in the angle of the light results in a greater energy loss. Therefore, a small difference between the refractive indices of the waveguide 110 and the fluorescent substance can help advantageously reduce loss of light energy and enhance performance. Selecting materials so that the waveguide 110 has a lower refractive index than the fluorescent substance can also help reduce refraction, thereby reducing energy loss and increasing efficiency. In some embodiments, the lower the concentration of the fluorescent substance, the greater the impact of the difference in refractive indices between the waveguide 110 and fluorescent substance on the amount of light lost and efficiency.

In some embodiments, the waveguide 110 can comprise a flexible tube or sleeve rather than a rigid tube made of, for example, glass. A diameter of a flexible waveguide 110 can change as the pressure of the fluorescent substance flowing through the waveguide 110 changes, similar to a balloon. A flexible material, for example, polytetrafluoroethylene (PTFE) can have a low index of refraction so that the waveguide 110 is more efficient and produces more output energy. Example materials for the waveguide 110, generally in order of decreasing refractive indices and therefore decreasing loss of light energy, include: a glass, for example LASF43 glass, sapphire, quartz, boro silicate, and AF-2400 Teflon® (polytetrafluoroethylene (PTFE)). In some embodiments having a waveguide 110 with a high refractive index, the difference in the refractive indices of the waveguide 110 and fluorescent substance can be reduced by selecting a fluorescent substance having a high refractive index, e.g., polyethylene glycol or silicon oil. A fluorescent substance having a higher refractive index can also allow for more fluorescent light to be captured in the waveguide 110 and fluorescent substance by means of total internal reflection, thereby amplifying light energy within the waveguide 110.

Figure 2:
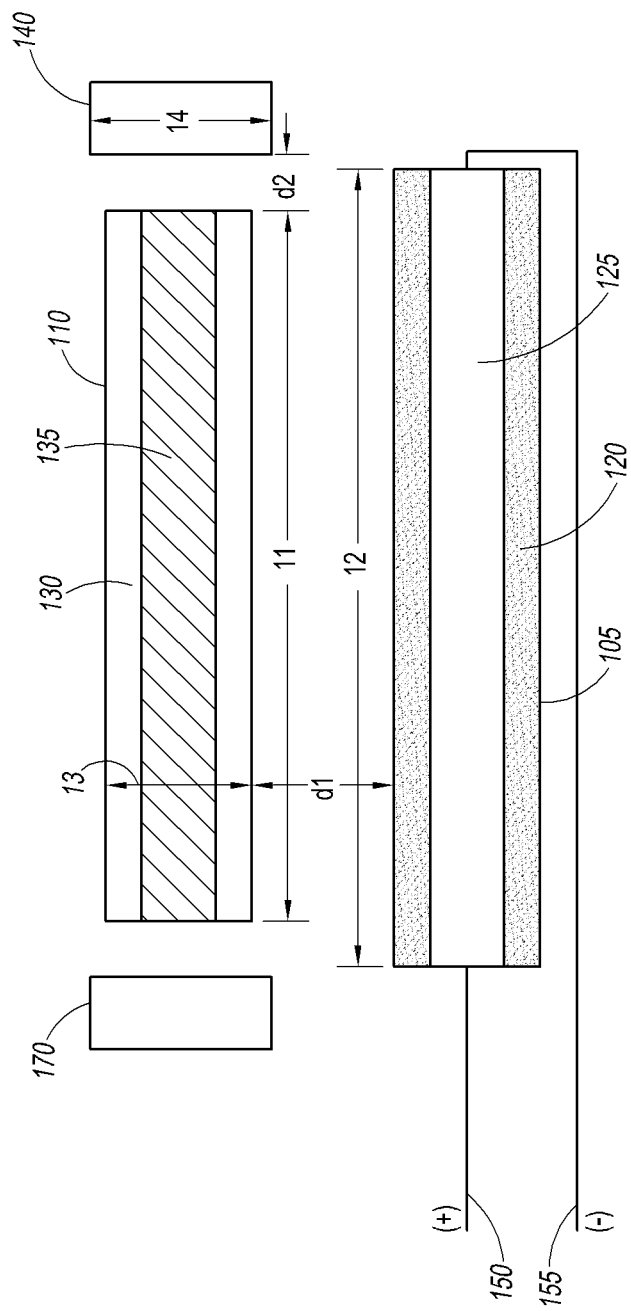
FIG. 2 illustrates an exemplary arrangement of some aspects of a fluorescent handpiece.

FIG. 2 illustrates an exemplary arrangement of various aspects of a fluorescent handpiece. In various embodiments, the waveguide 110 is separated by a distance d1 from the source 105, which can mitigate heating of the waveguide 110 and the fluorescent substance by the source 105 by mitigating the thermal communication between the source 105 and the waveguide 110. The separation distance d1 can also mitigate heating by facilitating a coolant, or other cooling element, to be disposed at least partially between the source 105 and the waveguide 110. In one embodiment, distance d1 can be about 1 mm to 100 mm, for example, 10 mm. In various embodiments, the waveguide 110 has a length l1, which can be greater than, less than, or equal to the length l2 of the source 105 (e.g., arc length, excluding the dimension of the electrodes), which can facilitate transmission of electromagnetic radiation to substantially the entire length of the waveguide 110 and/or maximize the use of the fluorescent substance. In one embodiment, length l1 can be about 1 mm shorter than the length l2 (e.g., 0.5 mm shorter at each end). In one embodiment, length l1 can be about 2 mm to 4 mm shorter than the length l2 (e.g., 1 mm to 2 mm longer at each end). In some embodiments, the waveguide length l1 can be greater than length l2 of the source 105. For example, the waveguide 110 can be sealed off and have an o-ring at each end. The o-ring end portions can each be about 1 mm in length, so that the total waveguide 110 length l1 is about 2 mm greater than length l2. The end portions of the waveguide 110 can be coated with a reflective or totally internally reflective coating to help reduce the loss of light from the waveguide 110 to the o-rings and to protect the o-rings from thermal damage. The coating can be, e.g., internal gold, internal silver, an optical coating, PTFE, or another low refractive index material. In various embodiments, the waveguide 110 is separated by a distance d2 from the skin contacting portion 140. In one embodiment, the distance d2 is about 0.5 mm. In various embodiments, the waveguide 110 has a diagonal length (e.g., a diameter) l3 that is less than a corresponding diagonal length l4 of the skin contacting portion 140. In one embodiment, length (e.g., a diameter) l4 is about two times distance d2 longer than length l3 (e.g., l4≈2d·2+l3), to direct the cone electromagnetic radiation emitted from waveguide 110 to the skin. However, the lengths l4 and l3 are not limited to this relationship and can be substantially the same, greater, or lesser.

In another embodiment, the waveguide 110 and the skin contacting portion 140 are substantially in contact. In one embodiment, the waveguide 110 and the reflector 170 are not in direct contact or are otherwise separated (e.g., intervened by a gas, liquid, or solid). This separation can facilitate cooling of the waveguide 110, for example, by increasing thermal communication between the waveguide 110 and a coolant or other cooling element. In some embodiments, the fluorescent substance can circulate or pass through the space between the waveguide 110 and reflector 170. This spatial separation can also be designed to optimize the reflection of electromagnetic radiation from a distal end of the waveguide 110, to the reflector 170, and back into the waveguide 110. In another embodiment, the waveguide 110 and the reflector 170 are substantially in contact. The relative positions, sizes, and/or optical properties (e.g., convexity/concavity/flatness) of the waveguide 110 and the reflector 170 can be designed to maximize the amount of electromagnetic radiation reflected back into the waveguide.

The fluorescent substance can be circulated by the system 115 through the waveguide 110, and is capable of modulating at least one property of the electromagnetic radiation. The system 115 can help extend the usable lifetime of the fluorescent substance by at least one of mitigating quenching of the fluorescent substance, mitigating bleaching of the fluorescent substance, mitigating heating of the fluorescent substance, and mitigating chemical reaction of the fluorescent substance. In some embodiments, the system 115 can include a particle filter. In some embodiments, the system 115 can be adjacent a port, which is in fluid communication with the system and adapted for receiving the fluorescent substance from a reservoir 160. In one embodiment, the port is adapted for receiving the fluorescent substance from a cartridge that is detachably connectable with the port. A cartridge can contain about 2 deciliters, or more, or less, of the fluorescent substance. In another example, the port can be adapted for receiving the fluorescent substance from another source such as an umbilicus that can be attached to the handpiece 100. A conduit 165 establishes a fluid communication between the waveguide 110, the system 115, and the port.

The system 115 can include a pump for circulating the fluorescent substance. The pump can be any type of pump suitable for a fluorescent substance, including a bellows, centrifugal, diaphragm, drum, flexible liner, flexible impeller, gear, peristaltic (e.g., tubing), piston, progressive cavity, rotary lobe, rotary vane, or syringe pump. In one embodiment, the pump is a magnetically-coupled gear-type pump. In another embodiment, the pump is a solenoid operated pump. In various embodiments, the pump can include a polytetrafluoroethylene (PTFE, for example TEFLON®, a registered trademark of E.I. du Pont de Nemours and Company) or a stainless steel material defining at least a portion of a circulation path of the fluorescent substance. PTFE, or a material with similar physical and chemical properties, can be used in the seals. Pump materials can be selected that are essentially chemically inert, for example, with respect to the fluorescent substance and the operating environment.

Figure 3:
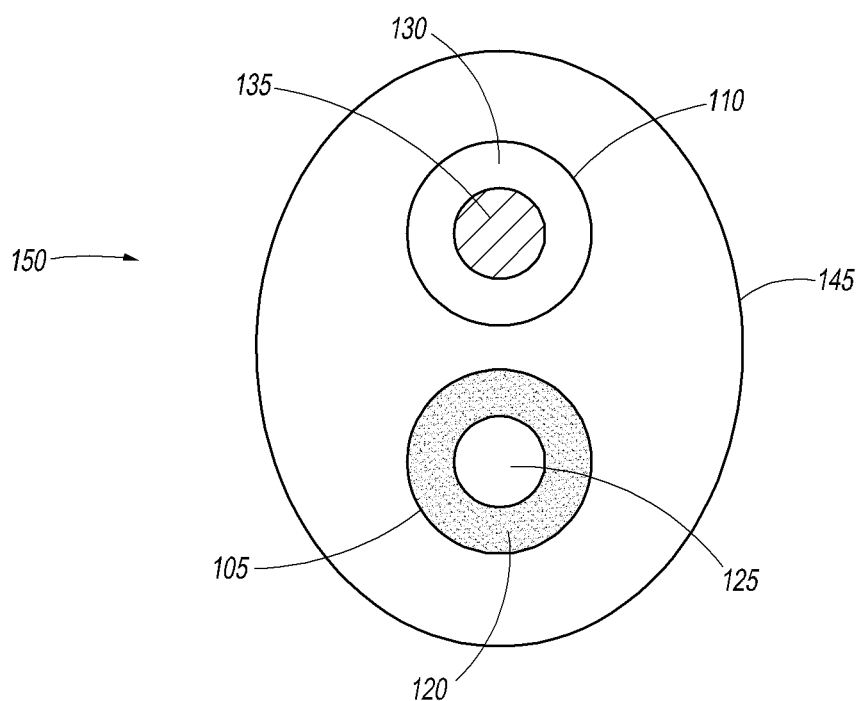
FIG. 3 illustrates another view of certain aspects of a fluorescent handpiece.

FIG. 3 illustrates a cross sectional view 150 of a portion of the fluorescent handpiece of FIG. 1. The source 105 can include a cover 120 and can have a gas in its interior 125. In one example, the gas is xenon. In general, the source 105 is selected to emit at least a wavelength of light employed by the fluorescent substance. In one embodiment, the passage 135 through the waveguide 110 has a diameter of about 2 mm to about 30 mm. In one embodiment, the thickness of the pipe 130 wall can be in the range of about 0.5 mm to about 2 mm. In general, the passage 135 has a diameter that is selected to contain a sufficient volume of fluorescent substance, the thickness of the pipe 130 wall is selected based upon the material to provide sufficient structural integrity, and the total diameter of the waveguide 110 is chosen with regard to the desired spot size to be produced by the handpiece 100. The total diameter of the waveguide 110 can also be chosen with regard to the dimensions of the source 105, the length of the waveguide 110, and the concentration of the fluorescent substance.

In general, the fluorescent substance is capable of modulating (e.g., transforming, converting, or varying) at least one property of the electromagnetic radiation. For example, the fluorescent substance can be a dye selected to convert the electromagnetic radiation from at least one first wavelength to at least one second wavelength. In some embodiments, more than one dye can be employed to utilize the light from the source 105. Accordingly, at least one dye can be selected depending upon the desired treatment and/or desired emission wavelength. Because the emission wavelength can be controlled by selecting one or more appropriate dyes, the fluorescent handpiece 100 does not require a filter to obtain the desired emission wavelength. However, in some embodiments, the fluorescent handpiece 100 can include a filter, for example an optical filter, for controlling the wavelengths delivered to the biological tissue. In some embodiments, a spatial filter is used to control the spot size and spot shape.

The absorbing and emitting wavelengths of the fluorescent substance can be selected by the user or a technician. In one example, the fluorescent substance can change blue-green light to yellow light. For example, the fluorescent substance can be a liquid dye such as pyrromethene, for example, pyrromethene 556, for changing light emitted from the source 105 to the desired wavelength. The concentration of the dye can be varied to achieve different wavelengths of output light. A suitable concentration can be a concentration sufficient to achieve about 70-100% absorption of electromagnetic bandwidth of the electromagnetic radiation from the source 105. The liquid base can be, for example, water, an alcohol, e.g., polyethylene glycol, a mixture of alcohols, for example, methanol and/or ethanol, or a mixture of alcohol and water. Other liquid bases, for example, an oil, such as silicon oil, or DMSO, are also possible. In various embodiments, the fluorescent substance can include 4-dicyanomethylene-2-methyl-6-(p(dimethylamino)styryl)-4H-pyran (DCM), pyrromethene, fluorescein, coumarin, stilbene, umbelliferone, tetracene, malachite green, rhodamin, rhodamin 6G, or Sulforhodamine 640 Chloride. In various embodiments, adamantine can be added to a fluorescent substance to prolong its life. In some embodiments, cycloheptatriene and cyclooctatetraene can be added to a fluorescent substance as triplet quencher, to increase output power. In certain embodiments, a fluorescent substance can include one or more pyrromethenes or other fluorescent dyes. The reflection index for the liquid can differ strongly from the reflection index in the waveguide 110, or can be substantially the same. A suitable flow rate for the liquid can be about 0.5-4 L/min. The passage 135 can be part of the system 115.

In various embodiments, the cooling system 145 can be a system for cooling the fluorescent substance. In some embodiments, the system 115 for circulating a fluorescent substance can function as, or include a, system for cooling the fluorescent substance. The cooling system 145 can also be adapted to cool any of the components of the handpiece 100, and/or to cool the biological tissue separately or in an integrated cooling system. The cooling system 145 can be in thermal communication with at least one of the source 105, the waveguide 110, the skin contacting portion 140, and the system 115. The cooling system 145 can employ a coolant such as a gas or liquid to cool at least one of the source 105, the waveguide 110, the skin contacting portion 140, and the system 115. In one embodiment, the cooling system 145 employs water as a coolant. In one embodiment, the cooling system 145 has an intake 175 and an exhaust 180, for receiving and removing coolant in the cooling system 145. In one embodiment, the cooling system 145 includes a Peltier, or thermo-electric cooler. The cooling system 145 can include a radiator or a fan.

In some embodiments, various components of the system can benefit from cooling, for example, the fluorescent substance, the source 105, and/or skin contacting portion 140 or output optic described in greater detail herein. Each of these components can have an associated cooling system, either separately or integrated with the others. The source 105 can be provided with its own cooling system due to the amount of heat produced by the source 105. In some embodiments, a cooling system cools the fluorescent substance, which in turn can cool the skin contacting portion 140 or output optic. In some embodiments, the waveguide 110 can have its own associated cooling system, for example, a water jacket. The various cooling systems can include a radiator, a fan, a heat-exchanger system, or any other cooling system described herein or otherwise known in the art.

U.S. Pat. No. 5,320,618, the disclosure of which is incorporated herein by reference in its entirety, teaches various sources, waveguides, systems, systems for cooling, and other aspects that can be readily adapted by one skilled in the art for use with the present invention.

In various embodiments, the electromagnetic radiation delivered to the biological tissue is characterized by a pulse width or exposure time between about 0.2 ms and about 60 min. In some embodiments, the electromagnetic radiation delivered to the biological tissue can be characterized by pulses of about 0.2 ms to about 500 ms with increments of about 0.2 ms. In some embodiments, a pulse width is between about 0.4 ms and about 100 ms. In some embodiments, a pulse width is about 1, 2, 3, 4, 5, 10, 15, or 20 s. The current system can produce light pulses having longer pulse widths than typical laser systems operating at the same wavelength. For example, the pulse width of some dye lasers is limited by triplet state formation. Laser systems also disadvantageously can cause adverse effects such as purpura, pain, PIH (post inflammatory hyperpigmentation), and/or revascularization. The electromagnetic radiation delivered to the biological tissue can be absorbed preferentially by a chromophore in the skin. For example, the chromophore can include at least one of hemoglobin in blood, melanin, pheomelanin, porphyrin, exogenous pigment, fat, and water in the skin. The chromophore can absorb the electromagnetic radiation preferentially over adjacent skin tissue. The spectrum characterizing the electromagnetic radiation delivered to the biological tissue can be matched to an absorption spectrum of at least one of whole blood, hemoglobin, reduced hemoglobin, and oxidized hemoglobin.

For example, in some embodiments, the electromagnetic radiation delivered to the biological tissue can have an intensity peak at a wavelength of about 544 nm and a full width at half maximum of about 530 nm to about 570 nm or about 529 nm to about 586 nm to approximate the absorption spectrum of hemoglobin. Such a light spectrum can advantageously be used to treat vascular lesions. One challenge in treating vascular lesions is the possibility of revascularization, which can cause treatment resistance and/or a need for multiple treatments. Revascularization can occur if endothelium is left not denaturized in the tissue after treatment. Revascularization can be caused, at least in part, by short pulses that explode the intima so that the vessel endothelium is not completely denaturized. Growth factors released as part of an inflammatory response to the injury can cause the vessel to re-grow from the non-denaturized endothelium cells. Electromagnetic pulses of more than 0.45 ms and up to 20 ms at the absorption bands of hemoglobin can allow for selective destruction of a more complete portion of the endothelium of the vessel to be removed to help prevent revascularization.

In some embodiments, the concentration of the dye can be varied to achieve different wavelengths of output light. For example, a higher concentration of pyromethene 556, for example, about 9.6 g/L, can produce yellow light having an intensity peak of about 575 nm. The fluorescent substance can also be selected to have a different concentration of a yellow emitting dye to produce green light substantially without yellow wavelengths and having intensity peaks at about e.g., 529 nm, 532 nm, or 535 nm. For example, a more diluted solution including pyromethene 556, for example, about 4.8 g/L, can produce green light. The fluorescent substance can also be selected to produce UVA, blue, orange, red, or NIR light. In some embodiments, a system as described herein can allow the wavelength peak to be tuned to wavelengths between about 450 nm and about 850 nm. In some embodiments, a system as described herein can allow the wavelength peak to be tuned to wavelengths between about 500 nm and about 670 nm. In some embodiments, the peaks can be overlapping or separate.

Electromagnetic radiation can also be delivered by scattering-depth determined deposition. For example, freckles of different shades (e.g., light, medium, and dark relative to surrounding skin) can be treated by different wavelengths of electromagnetic radiation (e.g., peaks of about 480 nm for light, about 515 nm for medium, and about 535 nm for dark). A light, shallow freckle may not have enough pigment to absorb enough electromagnetic radiation to be effectively treated. By using a shorter wavelength, electromagnetic radiation can scatter more in the tissue and penetrate less through the tissue, which can result in a longer path and more absorption within the freckle. In another example, a thicker, deeper (e.g. dermal) blood vessel can be treated by a relatively longer wavelength, which can reach within the dermis, and a thinner, shallower blood vessel can be treated by a relatively shorter wavelength. In one embodiment, a thicker vessel can be treated by electromagnetic radiation in the range of about 555-595 nm and a thinner vessel can be treated by electromagnetic radiation in the range of about 515 to 555 nm. For another example, resistant port wine stains are often seen in infants or juveniles with little melanin and are typically found in a shallow portion of the vessel bed. To treat such port wine stains, the wavelength of light delivered to the tissue can be selected to have a shorter wavelength so that the energy penetrates less and more effectively treats the shallow part of the juvenile port wine stain.

The electromagnetic radiation delivered to the biological tissue can be characterized by a spot size between about 1 mm and about 40 mm. A spot size can be up to about 1, 2, 3, 4, 5, 6, 7, 8, 9, 10, 11, 12, 16, or 20 mm in diameter. In various embodiments, the handpiece can produce a spot size of about 2 mm or greater in diameter. In general, the optical diameter of the waveguide and the skin contacting portion are proportional to the diameter of the spot size when the skin contacting portion is in contact with the skin. The spot can be various shapes, for example, rectangular, quadratic, round, or elliptical. The spot size can be changeable by means of, for example, an exchangeable extension of the skin contacting element, and/or an exchangeable spatial filter.

The electromagnetic radiation delivered to the biological tissue can be characterized by an energy density between about 0.1 J/cm$^2$ and about 500 J/cm$^2$. In various embodiments, the electromagnetic radiation delivered to the biological tissue can be characterized by an energy density between about 1 and about 100 J/cm$^2$, about 2.5 J/cm$^2$ and about 60 J/cm$^2$, or about 2.5 J/cm$^2$ and about 20 J/cm$^2$. In certain embodiments, the energy density can be about 1, 5, 10, 50, 100, 150, 200, 250, 300, 350, 400, or 450 J/cm$^2$. In some embodiments with skin exposure time of longer than about a few seconds can have fluences higher than 450 J/cm$^2$. The handpiece can include means for tuning a pulse width and/or fluence characterizing the electromagnetic radiation delivered to the biological tissue.

Figure 4:
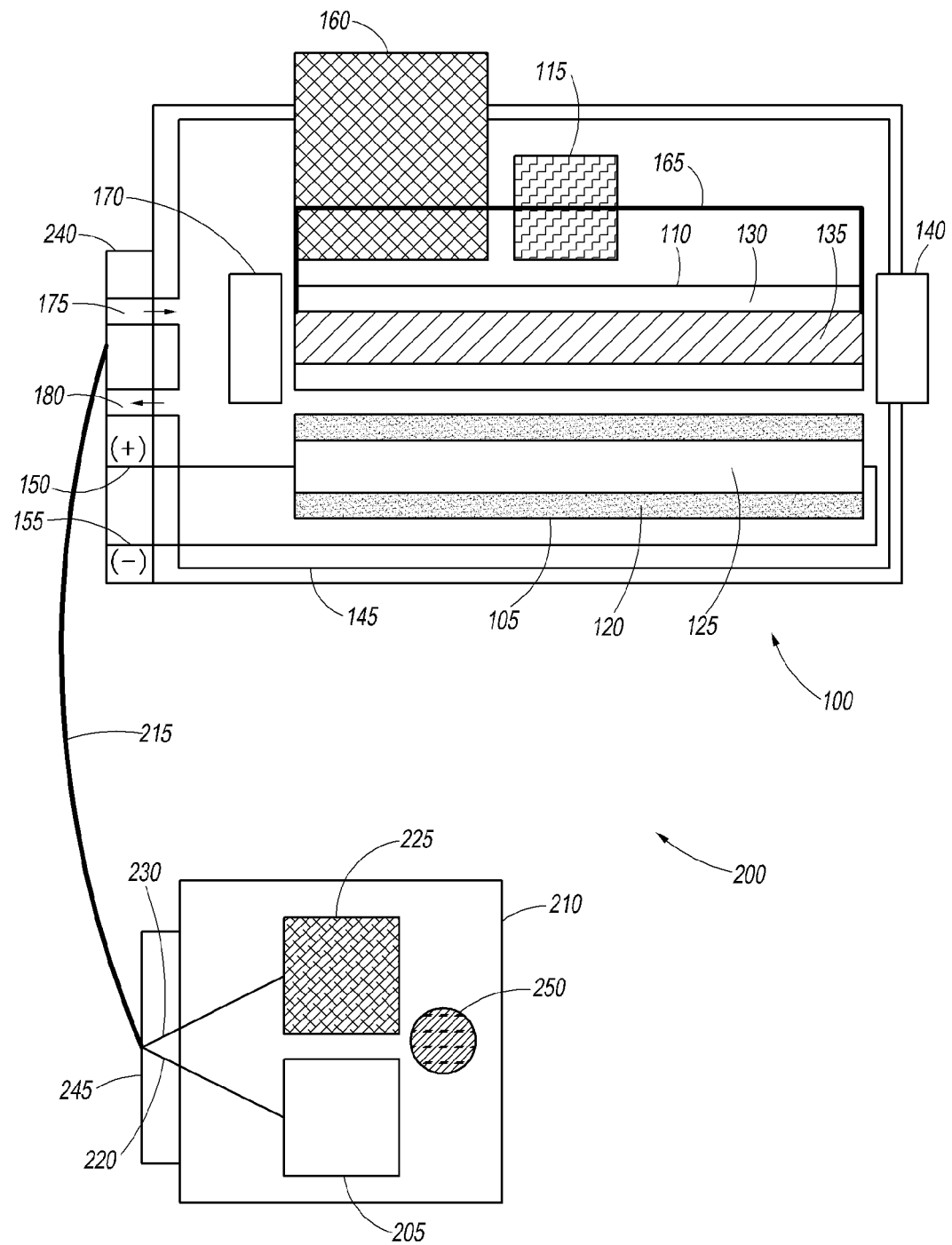
FIG. 4 illustrates an embodiment of an apparatus for treating biological tissue.

FIG. 4 illustrates an embodiment of an apparatus 200 for treating biological tissue. The apparatus 200 includes a fluorescent handpiece 100 that can include the features described in connection with FIG. 1. The apparatus 200 also includes a base unit 210 that can include at least one of an energy 205 source, a coolant 225 source, and a controller 250. The base unit 210 can be connected to the fluorescent handpiece 100 by an umbilicus 215. The umbilicus 215 includes a first 240 point of connection between the umbilicus 215 and the handpiece 100, and a second 245 point of connection between the umbilicus 215 and the base unit 210. The umbilicus 215 can include a power 220 conduit for transmitting energy from the energy 205 source to the source 105 of electromagnetic radiation via a circuit established through the positive 150 and negative 155 terminals. The umbilicus 215 can also include a coolant 230 conduit that establishes coolant communication between the fluorescent handpiece 100 and the base unit 210.

In various embodiments the cooling system 145 can cool the fluorescent substance and/or other components of the handpiece 100. The cooling system 145 can be adapted for cooling biological tissue. The base unit 210 can include a coolant 225 source that can deliver coolant to the cooling system 145 through a coolant 230 conduit. The coolant 230 conduit travels through (or along or on the outside of) the umbilicus to the cooling system 145 via a delivery or circulatory system established through the intake 175 and, if necessary, an exhaust 180. In some embodiments the coolant 230 conduit facilitates coolant flow only to (e.g., in the case of a gas that can be vented) or both to and from (e.g., in the case of fluid that can be circulated) the handpiece 100. In certain embodiments, the coolant 225 source includes means to control and/or circulate the coolant, and the coolant 230 conduit and cooling system 145 are simply channels. In one embodiment, the cooling system 145 can control and/or circulate the coolant. In one embodiment, the apparatus 200 includes a radiator or heat exchanger in the handpiece 100 or the base unit 210.

In some embodiments, the apparatus 200 includes a controller 250 for controlling at least one of the energy 205 source, the coolant 225 source, the cooling system 145, and the source 105.

FIG. 4 illustrates a first 240 point of connection between the umbilicus 215 and the handpiece 100, and a second 245 point of connection between the umbilicus 215 and the base unit 210. In some embodiments, these points of connection are essentially fixed at the time of manufacture or assembly and are not detachable without specialized tools. However, in various embodiments, these points of connection are easily and quickly detachable and reattachable without specialized tools. In some embodiments, the first 240 point of connection is detachable and reattachable such that a practitioner or technician can easily and quickly change handpieces in a clinical situation. For example, the apparatus can also include a first connector associated with the second end of the umbilicus and a second connector associated with the handpiece, the second connector detachably connectable to the first connector. In various embodiments, the handpiece includes a connector adjacent a first portion of the handpiece, for connecting the handpiece to an umbilicus and for receiving energy from a conduit in the umbilicus, the energy for driving the source of electromagnetic radiation. The connector can be adapted to receive a fluorescent substance from the umbilicus and is in fluid communication with the system for circulating or passing the fluorescent substance through the nonlinear waveguide. This has the advantage of allowing multiple handpieces to be used with a single base unit 210 and/or single umbilicus 215. Likewise, in some embodiments, the second 245 point of connection is detachable and reattachable such that the base unit is detachable from the umbilicus. U.S. patent application Ser. No. 11/800,663, the disclosure of which is incorporated herein by reference in its entirety, teaches various detachable handpieces and connectors that can be readily adapted by one skilled in the art for use with the present invention.

Figure 5:
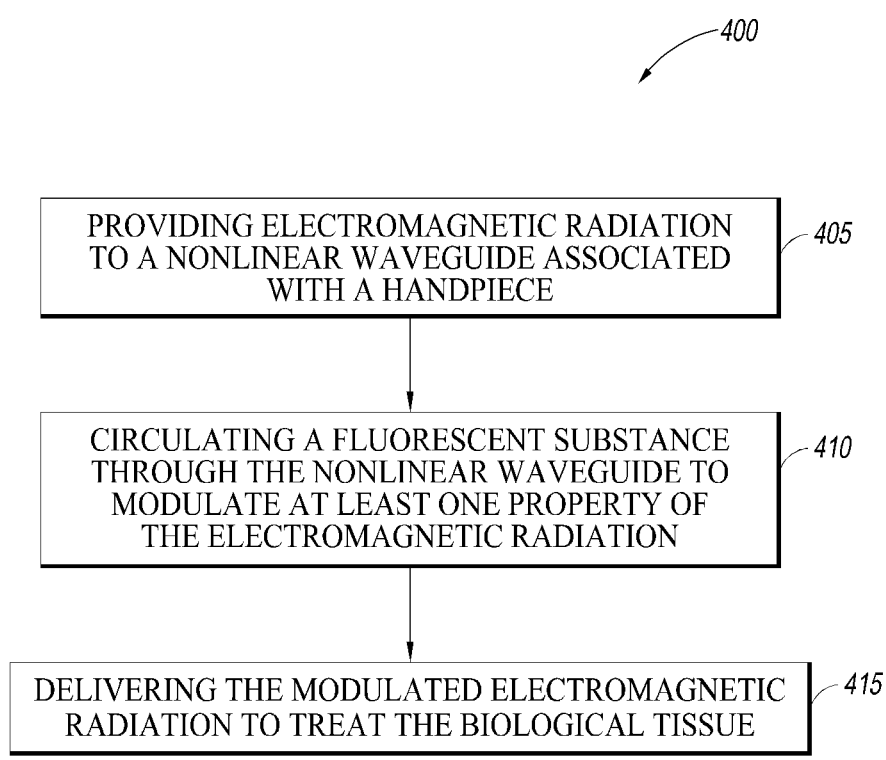
FIG. 5 illustrates a method for treating biological tissue using a fluorescent handpiece.
Figure 6A:
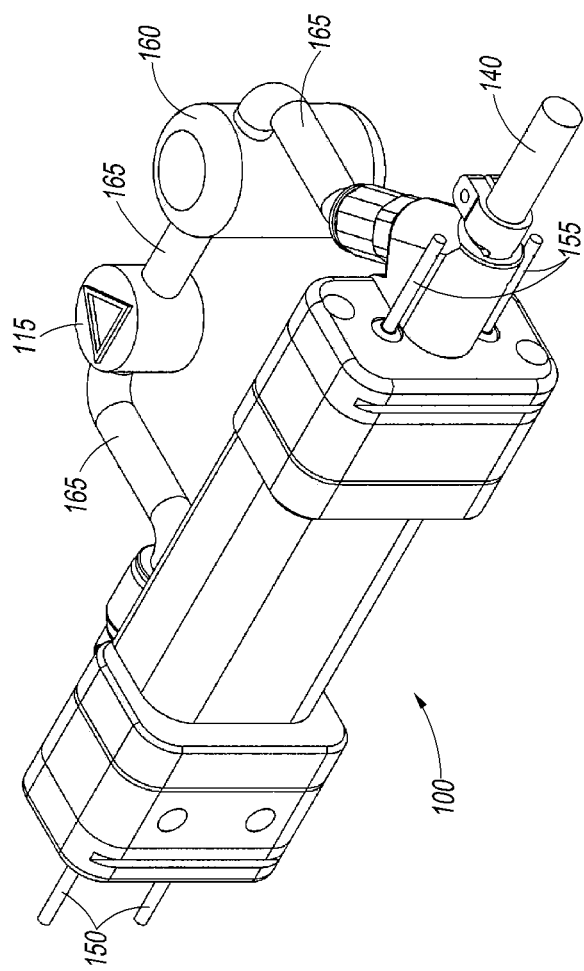
FIGS. 6A-D illustrate the exemplary embodiments of FIGS. 1-4, in 3D renderings produced by CADD-type software.
Figure 6B:
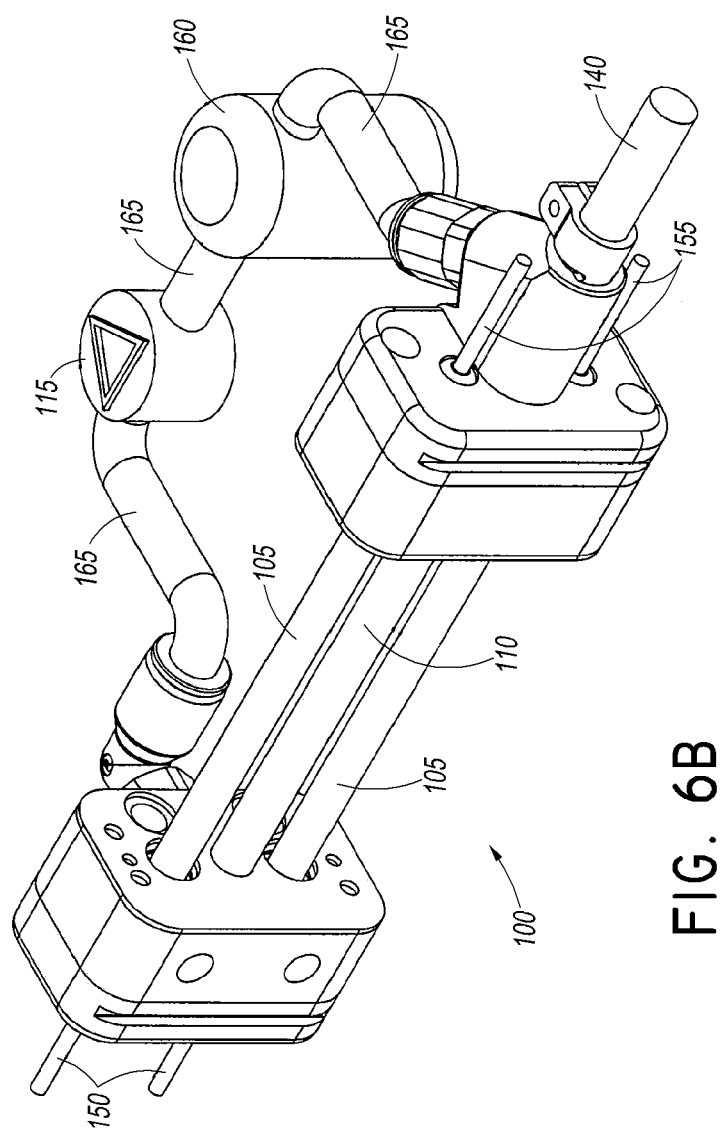
Figure 6C:
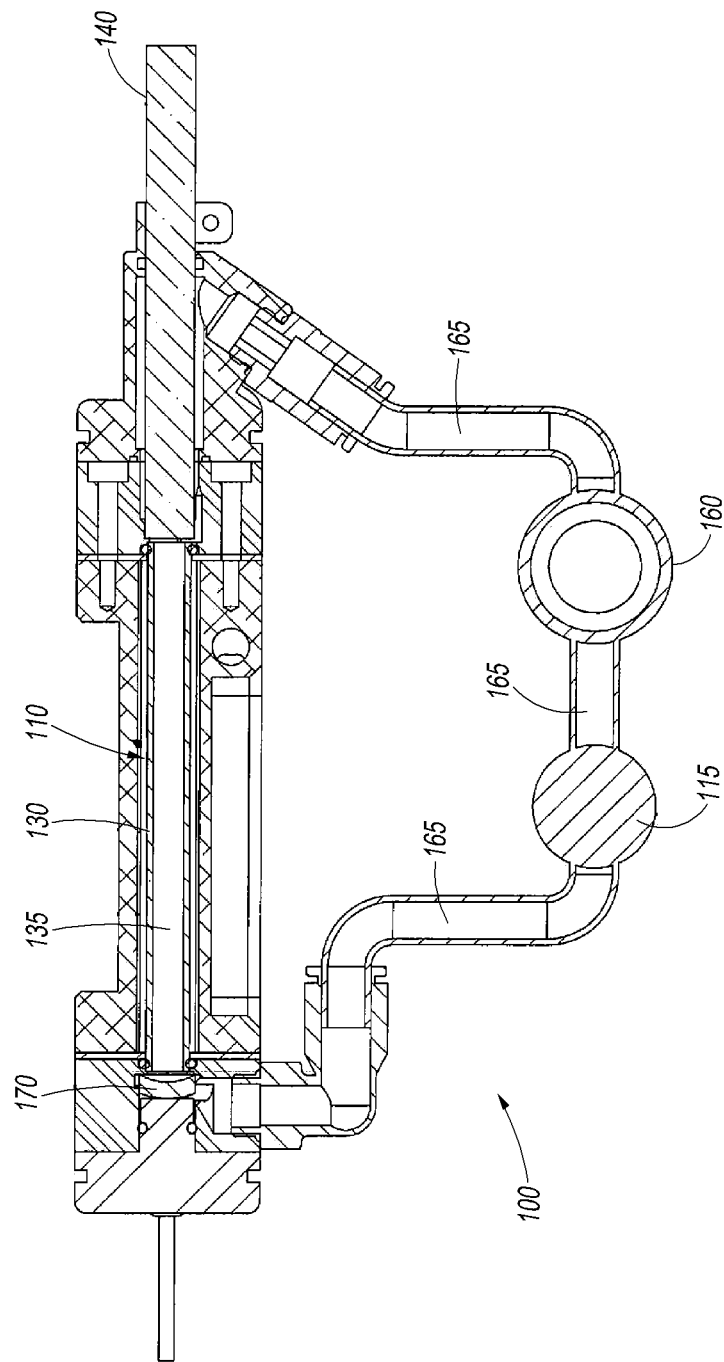
Figure 6D:
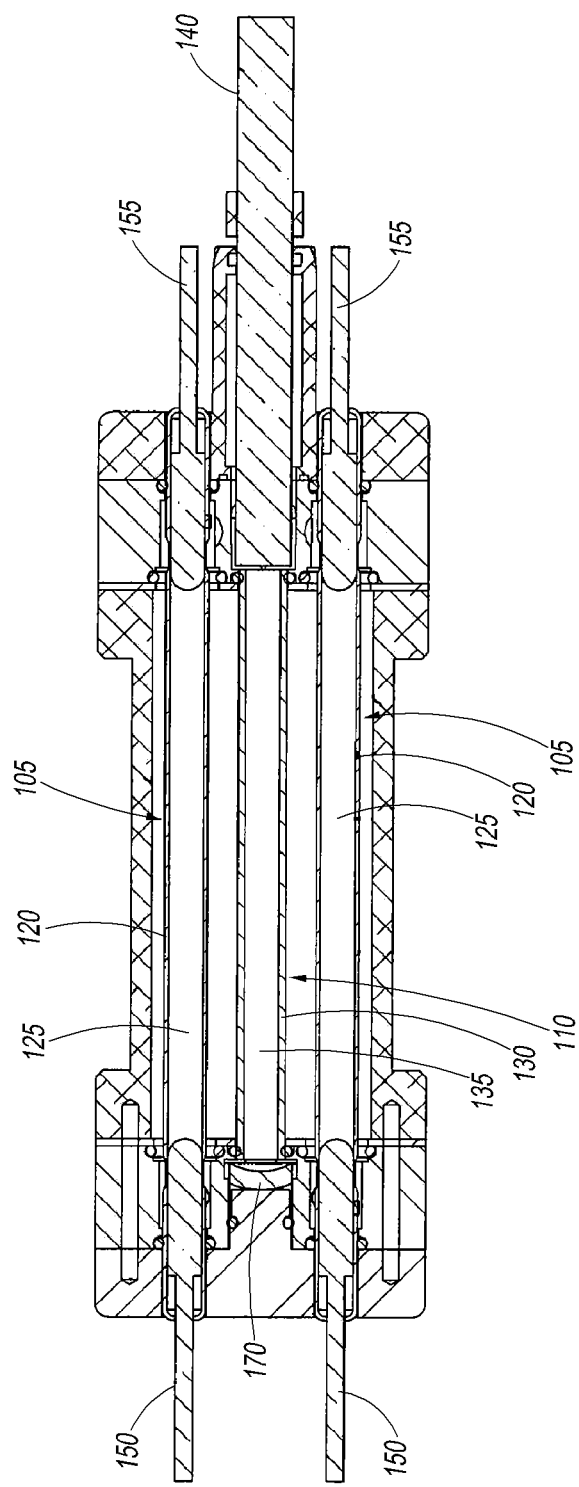

FIG. 5 illustrates a method 400 for treating biological tissue using a fluorescent handpiece. Step 405 includes providing electromagnetic radiation to a nonlinear waveguide associated with a handpiece. The handpiece can include aspects described in connection with FIGS. 1-4. Step 410 includes circulating or passing a fluorescent substance through the nonlinear waveguide to modulate at least one property of the electromagnetic radiation. Modulating at least one property of the electromagnetic radiation can include varying at least one of a wavelength, fluence, pulse or pulse train width, and pulse or pulse train shape associated with the electromagnetic radiation. Step 415 includes delivering the modulated electromagnetic radiation to treat the biological tissue.

In some embodiments, the method 400 includes treating skin having at least one of a superficial vascular lesion, port wine stain, telangiectasia, spider angioma, cherry angioma, rosacea, "diffusive red," poikiloderma, post-operative bruising, venous lakes, small vessel diameter lesion, arterial lesion, capillary lesion, venous lesion, pigmented lesion (e.g., benign epidermal pigmented lesions, benign pigmented dermal lesions, Becker's nevus or acquired nevus of Hori), tattoo, acne, psoriasis, vitiligo, and the like. The method 400 can also include treatments for wrinkles, for skin rejuvenation, fat removal, cellulite, body sculpting, decreasing circumference of a body part, for hair removal, and for hair regrowth. In certain embodiments, the method 400 includes delivering the electromagnetic radiation to the biological tissue in a train of pulses to gradually heat a region of the biological tissue to be treated.

FIGS. 6A-D illustrate the exemplary embodiments of FIGS. 1-4, in 3D renderings produced by CADD-type software. The reference numbers in FIGS. 6A-D correspond to the elements discussed in connection with FIGS. 1-4.

Figure 7:
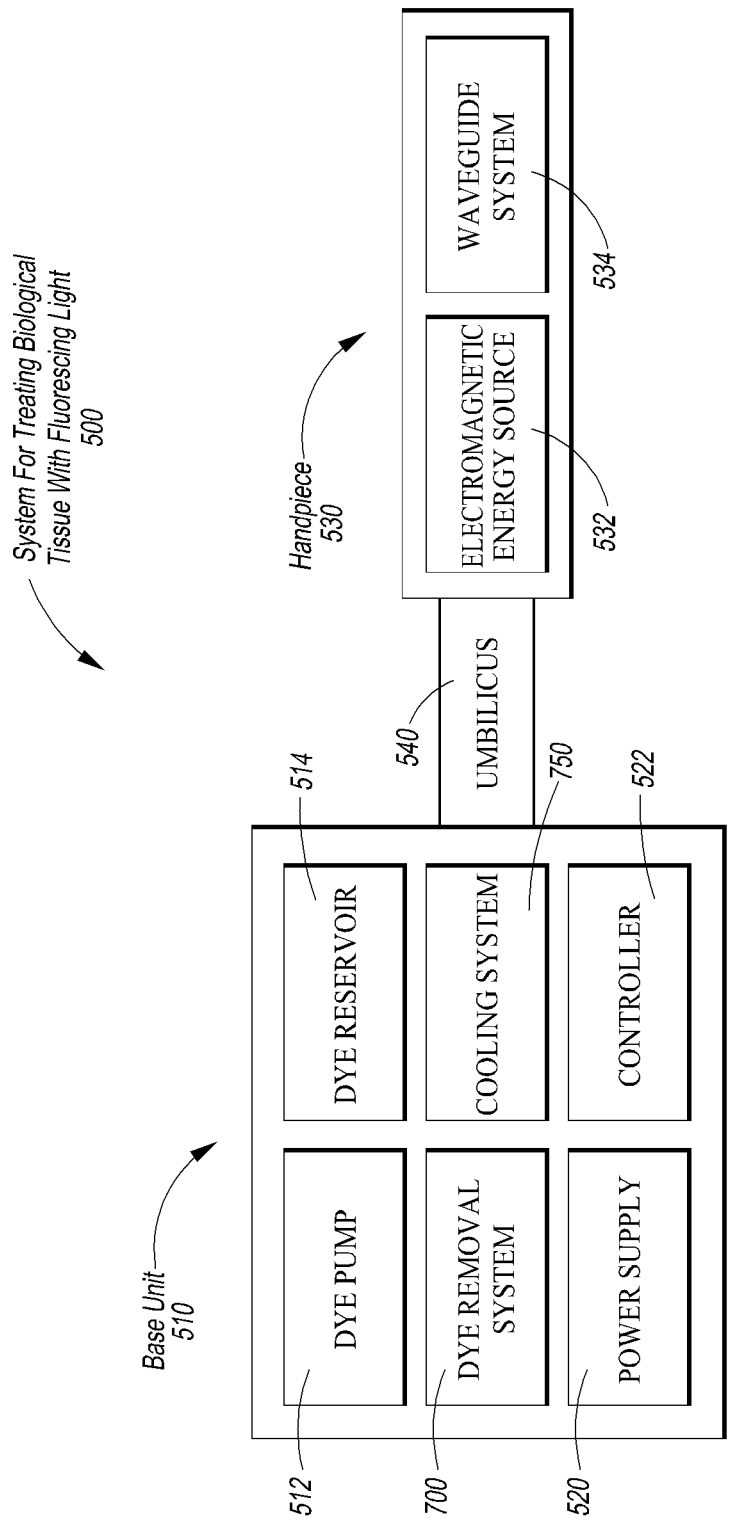
FIG. 7 illustrates another embodiment of a system for treating biological tissue with fluorescent light.

FIG. 7 illustrates another embodiment of a system 500 for treating biological tissue with fluorescent light. The system includes a base unit 510 and a fluorescing handpiece 530. An umbilicus 540 connects the handpiece 530 to the base unit 510. The base unit 510, handpiece 530, and umbilicus 510 are similar to, and include many of the same features as the base unit, handpiece and umbilicus described above with respect to FIGS. 1-5.

In the present embodiment, the base unit 510 includes a system, such as a dye pump 512, a dye reservoir 514, a dye removal system 700, a cooling system 750, a power supply 520 and a controller 522. The base unit 510 may also include a user interface and safety interlock system (not shown). In some alternative embodiments, one or more of a dye pump 512, a dye reservoir 514, a dye removal system 700, a cooling system 750, a power supply 520 and a controller 522 can be located in the handpiece 530.

The handpiece 530 includes an electromagnetic energy source 532 and a waveguide system 534. The umbilicus 540 includes electrical and fluid conduits to allow circulation or passing of dye and cooling fluid, and delivery of electrical energy, from the base unit 510 to the handpiece 530. In some embodiments, the electromagnetic energy source 532 is located in the base unit 510, and the umbilicus 540 includes a delivery system, for example, a light guide such as an optical fiber, optical fiber bundle, or a waveguide, for example, a liquid or partially liquid or hollow waveguide, or other means to transfer energy to the waveguide system 534 in the handpiece 530. In some embodiments, the source 532 can be, for example, a laser, a green laser, a lamp, or a diode laser.

The dye reservoir 514 may include a tank in which a fluorescing dye solution is stored. The dye solution may be formed by combining a dye pellet, powder, or liquid drops with a solvent, such as water. The dye solution is formed as the dye pellet, powder or drops dissolve into the water. In some embodiments, the dye reservoir 514 includes a device to facilitate dye dissolution. For example, the dye reservoir 514 may include a mixer or stirrer. In one embodiment, a piezoelectric vibrating membrane is provided to help facilitate dye solution formation. In another embodiment, a magnetic stirring device is provided. In other embodiments, a motorized blade spins to facilitate dye formation. In some embodiments, the current speed and/or direction of the dye solvent helps facilitate dissolution. The device to facilitate dye dissolution may be provided with the reservoir itself or at any other location in fluid communication with the dye reservoir.

For example, in some embodiments, the dye pellet, powder, or liquid is introduced by changing the entire dye reservoir 514, or by adding the dye in the handpiece 530, the base unit 510, or in the umbilicus 540. For example, the dye may be packaged within a cartridge that is inserted into a housing located within the handpiece 530, the base unit 510, or the umbilicus 540. In some embodiments, a dye pellet can weigh less than a gram and can last for about or greater than 70,000 pulses in use when dissolved in a 1 liter solvent reservoir.

A listing of dyes, solvents, and additives useful with the present invention is provided in attached Appendix A. Certain dye solutions, for example, water-based dyes, can be selected to result in a non-hazardous solvent system that is at least one of non-flammable or non-toxic and so as to not require hazardous waste disposal of the solvent. In some embodiments, two or more dye pellets, powders, or liquids can be used so that the circulating or passing dye solution includes a combination of dyes. The dyes can be selected so that one or more of the dyes drive one or more of the others. For example, one dye can be configured to absorb light from the light source and emit a wavelength of light that is better absorbed by another dye. In some embodiments, more than one dye can be introduced into the solvent so that more than two peaks, or portions of more than two peaks, are emitted from the waveguide.

Figure 8:
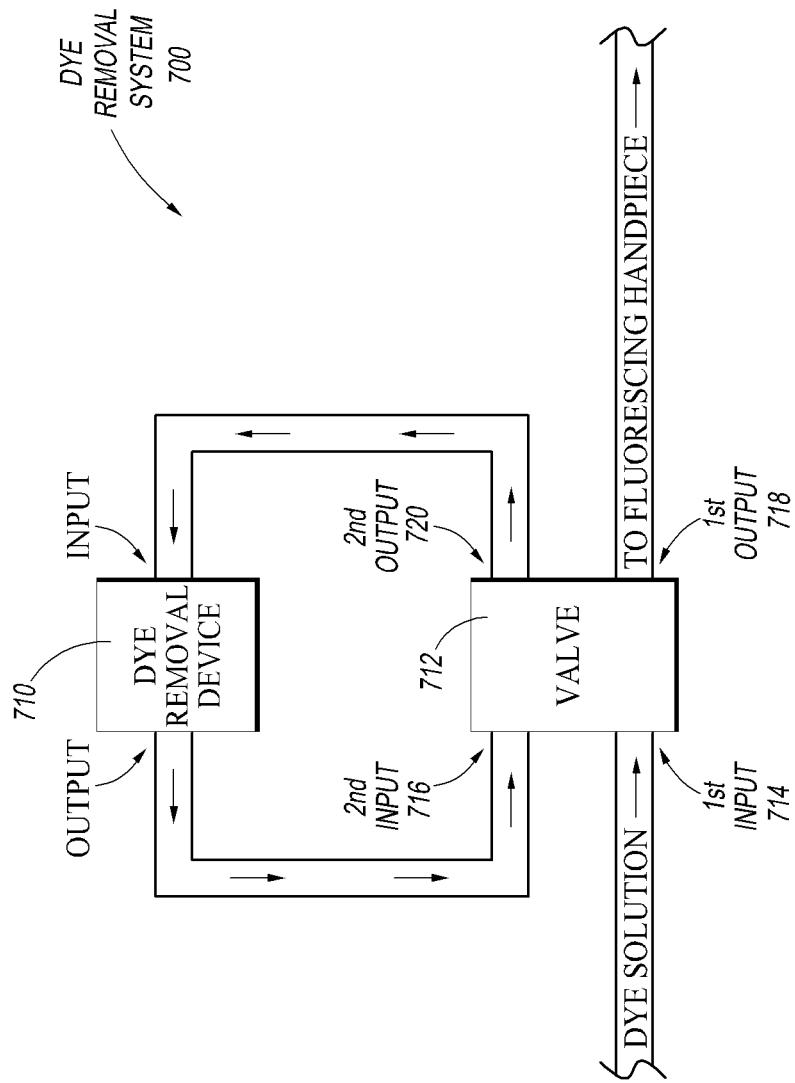
FIG. 8 illustrates one embodiment of the dye removal system of FIG. 6.

One embodiment of a dye removal system 700 is illustrated in FIG. 8. The dye removal system 700 allows the user to quickly and safely, manually or automatically, remove the dye from the dye solution. Once removed, the dye may be manually or automatically replaced with the same or a different dye pellet, solution, powder, etc. For example, if a user desires to change the therapeutic wavelength of light emitted from the fluorescing handpiece, the user may select a dye solution corresponding to the desired wavelength. In addition, if the user desires to change the therapeutic wavelength, he or she may activate a control at a user interface to cause automatic dye removal and replacement. A specific dye may be selected to obtain a therapeutic light from the handpiece having a specific, desired wavelength.

The dye removal system 700 is designed to direct the dye solution from the reservoir 514 to a dye removal device 710 upon user activation. In one embodiment, the dye removal system 700 includes a bypass valve 712, such as a 3-way or 4-way valve. The bypass valve 712 includes first 714 and second 716 inputs and first 718 and second 720 outputs. Dye solution is received by the bypass valve 712 at its first input 714 and prior to dye removal activation, is directly sent to the bypass valve's first output 718. The dye solution is sent to the fluorescing handpiece from the bypass valve's first output 718.

However, when the user desires to change the wavelength of light emitted from the fluorescing handpiece or if the dye solution has lost its effectiveness and needs to be changed, the user activates the dye removal system 700. When activated, dye solution is directed by the bypass valve 712 from the first input 714 to the bypass valve's second output 720 and to a dye removal device 710. The dye removal device 710 is configured to mechanically, electrically, magnetically, and/or chemically remove the dye from the dye solution. For example, in one embodiment, the dye removal device 710 includes a deionization filter configured to remove dye ions from the dye solution. When dye ions are removed from the dye solution, only substantially clear water remains in the dye solution. The clear water is provided from the dye removal device 710 to the bypass valve's second input 716, from which it is directed to the bypass valve's first output 718. From the first output 718 the clear water circulates or passes through the entire dye solution fluid loop (including through the handpiece), and is collected as clean, clear water in the base unit's reservoir 514. The bypass valve 712 advantageously allows for the dye solution to be rerouted to the dye removal device without introducing air bubbles into the solution. The bypass valve 712 further allows for removal of the dye outside the main fluid loop so that only clean water is reintroduced into the main loop ready to receive a new dye pellet, powder, or drops. In some embodiments, the dye solutions passes through the dye removal device 710 more than once to more completely purge the dye from the solvent. In some embodiments, the deionization filter can last for about or longer than 20 years. In some embodiments, the deionization filter can last for about or longer than 1 year.

In another embodiment, the dye removal device 710 includes a polarity filter, for example, an activated carbon filter, configured to remove polar dye molecules from the dye solution. Because water is a polar molecule, water (and other polar solvents) can dissolve both ionic and polar molecules. However, a deionization filter cannot remove polar but non-ionic molecules from the dye solution. In some embodiments, the dye removal system 700 is partially or entirely housed in a cartridge configured to be removably coupled to the base unit 510 and/or handpiece 530. This advantageously allows the user to select a dye removal system 700 including the appropriate dye removal device 710, e.g., one or more of a deionization filter, polarity filter, etc., for the particular dye (or dyes) to be removed from the dye solution. In some embodiments, multiple dye removal devices 710 of the same or different types can be coupled in series. In some embodiments, the valve 712 passes the dye solution first through one dye removal device 710 and then through at least one more dye removal device 712.

In some embodiments, the dye removal system 700 can function in a two-step process. At least one compound can be added to the dye solution to facilitate the removal of the dye by filtration. The dye solution including the compound can then pass through the dye removal device 710. For example, in some embodiments, chelants can be added to the dye solution. Chelants are chemicals that can form soluble, complex molecules with, e.g., certain metal ions, forming a chelate complex and inactivating the ions. The chelants added can have a high affinity for the dye molecules, ions, and/or polar molecules. Chelation can promote the formation of clusters of ions or molecules, which can facilitate filtering of the dye ions or polar dyes molecules. Other compounds can be added to the dye solution in addition to or instead of chelants.

After a predetermined time period, e.g., 30, 60, 90, 120, 300, or 600 seconds, substantially all of the dye has been removed from the dye solution, and the user may add a different dye pellet, powder, or drops to the reservoir 514 or anywhere else in the passage of dye solution in order to change the therapeutic wavelength of light to be emitted from the fluorescing handpiece. In other embodiments, a sensor is included in the dye solution flow path to detect the presence of dye within the dye solution. For example, in some embodiments a color sensor is used. When the sensor does (or does not) detect the color of the dye, the system indicates that the dye has not (or has) been removed from the dye solution. In some embodiments, a conductivity sensor can be used.

In other embodiments, a sensor includes an emitter that emits a light absorbed by the dye and a detector that detects the emitted light. If the dye is present in the dye solution, the sensor will not detect the emitted light; otherwise, it will. Such a sensor may be used to determine whether adequate dye removal has occurred such that a new dye may be added.

In some embodiments, the bypass valve 712, as well as the tubing used to carry the dye solution, is made from one or more of Delrin, PTFE, TUV and/or stainless steel. Other types of tubes, such as polyethylene tubes can sometimes release contaminating substances into the dye solution, which can destroy its usefulness as a fluorescing medium.

In some embodiments, the controller 522 can be programmed to allow for automatic changing and/or refreshing of the dye. For example, a sensor can detect when the dye drops below a certain density, concentration, color level, etc. and provide a control signal or input to the controller regarding the dye condition. The controller can then automatically cause more dye to be released into the solution from a cartridge, reservoir, or another source. The controller can also automatically cause dye of a different wavelength to be added to the reservoir solution. Mixing dyes of different colors can cause the fluorescing light to include two or more primary wavelengths. In addition, the controller can also automatically activate the valve 712 to cause removal of the dye from the system. When the valve is activated, the solution flow is routed through the filter, which removes the dye from the solution. In some embodiments, the user can select from multiple cartridges, reservoirs, bins, etc. containing different dyes via a user interface, and the controller can then release the selected dye into the solution. In some embodiments, the user may be able to program the controller to automatically remove the dye in the solution and inject another dye after a certain period of time or when certain conditions are met.

Figure 9:
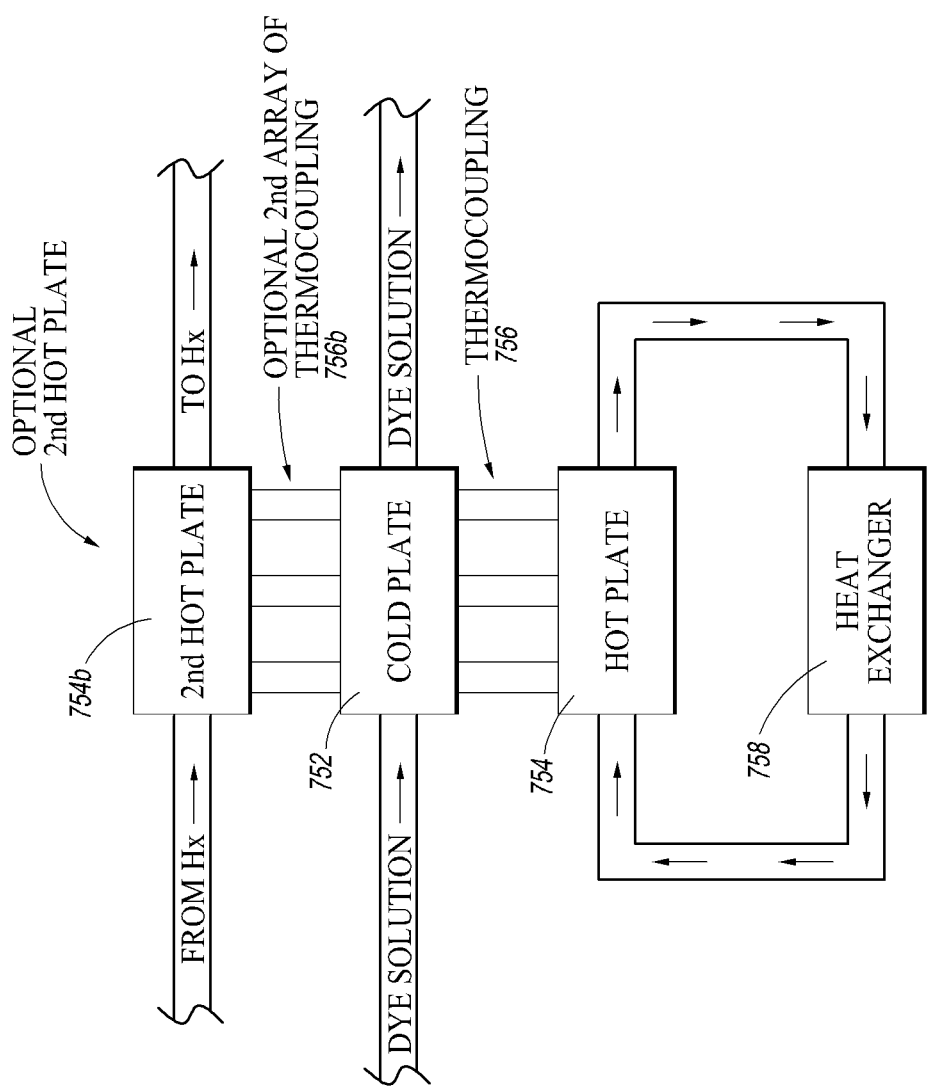
FIG. 9 illustrates one embodiment of the cooling system of FIG. 6.

One embodiment of a cooling system 750 is illustrated in FIG. 9. The cooling system 750 is configured to cool the dye solution prior to or after delivery to the fluorescing handpiece. The cooling system 750 includes a cold plate 752, a hot plate 754, a thermocoupling 756 between the cold plate 752 and the hot plate 754, and a heat exchanger 758. The cold plate 752 includes a thermally conductive material having a flow path into which the dye solution is directed. Heat from the dye solution is carried by the thermally conductive material to the hot plate across a thermocoupling 756. In one embodiment, the thermocoupling 756 includes a thermoconductive paste. In another embodiment, the thermocoupling 756 includes one or more, or an array of thermoelectric coolers. The thermoelectric coolers help draw the heat out of the dye solution and into the hot plate 754. The hot plate circulates a cooling fluid (e.g., water, methanol, ethylene glycol, propylene glycol, etc.) in a closed-loop system with a heat exchanger 758. In one embodiment, the heat exchanger 758 includes a radiator, pump, and a fan. Fluid from the radiator enters the hot plate 754 and is warmed by the heat absorbed from the cold plate 752 via the thermocoupling 756. The warm fluid circulates back to the radiator where it is cooled as it flows through the radiator's cooling fins, which are cooled by air blown with the fan.

In one embodiment, the cooling system includes two or more hot plates. For example, in one embodiment, the cooling system includes one hot plate on opposite sides of the cold plate (see FIG. 8). Fluid circulates through the second hot plate 754b and through the heat exchanger 758, as described above. In one embodiment, the cooling system cools the dye solution to about 1° C., 5° C., 10° C., 14° C., or room temperature.

In one embodiment, the power supply 520 is an electrical network configured to deliver electrical energy to drive the electromagnetic energy source 532 located within the handpiece 530. For example, in some embodiments, the power supply 520 includes one or more of a high-voltage power supply, capacitor, inductor, battery, autotransformer, energy stored as kinetic energy and released as electrical energy, energy stored as chemical energy and released as electrical energy, pulse forming network, switching components, IGBT transistor, MOSFET, etc.

In one embodiment, the controller 522 includes a microprocessor configured to drive the electromagnetic energy source, for example, by activating and deactivating the components of the power supply. The controller 522 may also include a user interface, such as a control panel and/or graphical user interface.

Figure 10:
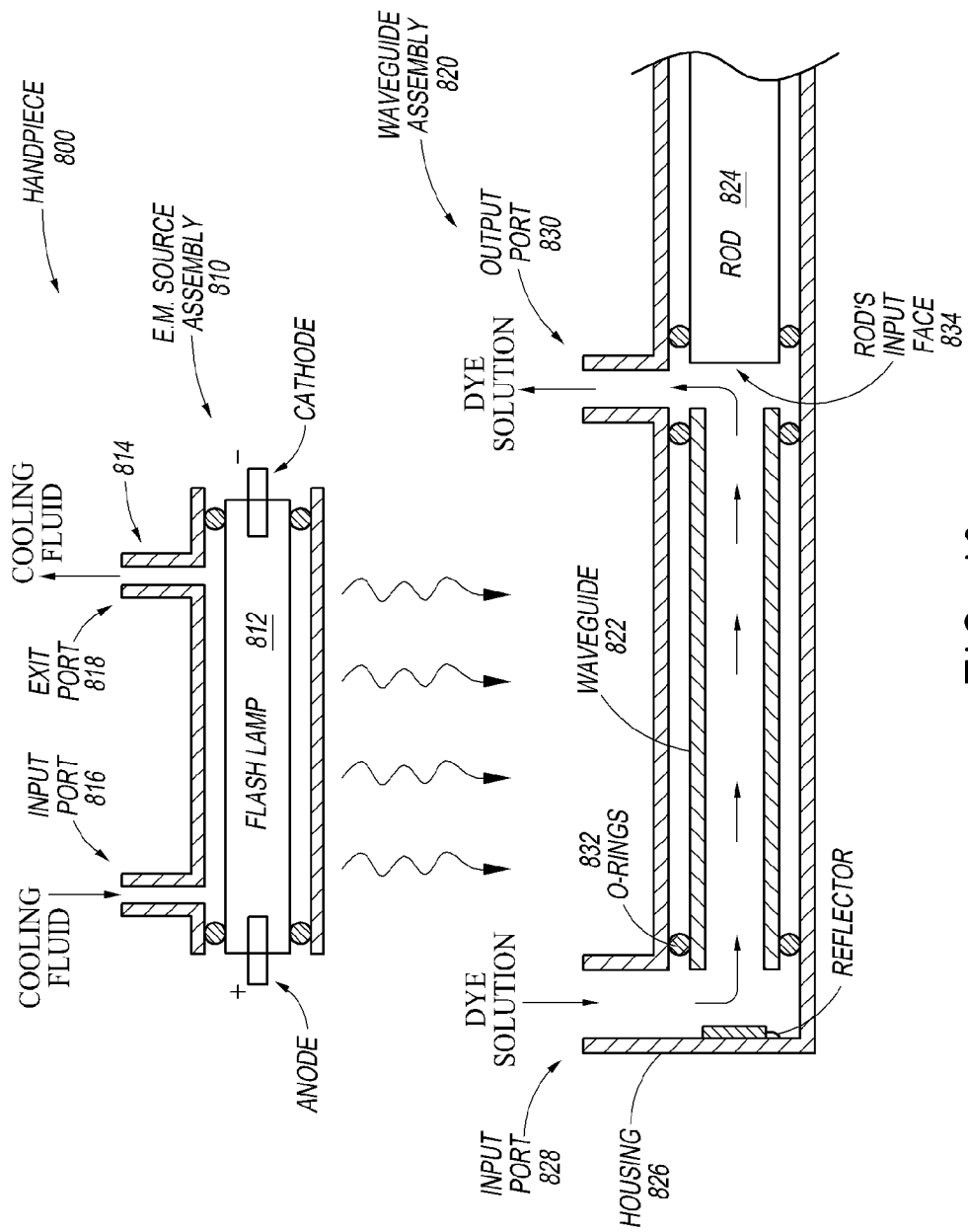
FIG. 10 illustrates one embodiment of the handpiece of FIG. 6.

One embodiment of a handpiece 800 is illustrated in FIG. 10. The handpiece 800 includes an electromagnetic energy source assembly 810 and a waveguide assembly 820. The electromagnetic energy source assembly 810 is shown as a flashlamp 812 enclosed within a flow tube 814. A cooling fluid enters the flow tube 814 at an input port 816, circulates around the flashlamp 812, and exits the flow tube 814 at an exit port 818. Light emitted from the flashlamp 812 is directed to a waveguide assembly 820. The waveguide assembly 820 may include a separate housing, or may be integrally formed with the flashlamp's flow tube 814.

In addition, the electromagnetic energy source may include any of a variety of optical devices, including but not limited to: an arc lamp, a Xenon arc lamp, a Krypton arc lamp, a Xenon-Krypton arc lamp, a flashlamp, a Xenon flashlamp, a Krypton flashlamp, a Xenon-Krypton flashlamp, a laser, a frequency-doubled Nd:YAG laser, a diode laser, a fiber laser, a fiber delivered laser, a dye laser, a Ruby laser, an Alexandrite laser, and/or a laser pumped laser.

In one embodiment, also shown in FIG. 10, the handpiece's waveguide assembly 820 includes a waveguide 822 and an output optic 824. In one embodiment, the output optic 824 includes a sapphire rod. In other embodiments, the output optic 824 can be a glass, for example, BK7 glass. Other materials are also possible. The waveguide 822 and output optic 824 are enclosed within a housing 826. Dye solution from the base unit enters the housing 826 at an input port 828, flows through the waveguide 822, and exits the housing 826 at an output port 830. The waveguide 822 and rod 824 are held in position within the housing 826 with o-rings 832. In addition, in the embodiment illustrated in FIG. 9, the output optic 824 (e.g., rod) has an optical input face 834 that is close to the housing's output port 830. Dye solution flows across and cools the rod's input face 834, but does not flow along the rod's axial length.

Figure 11:
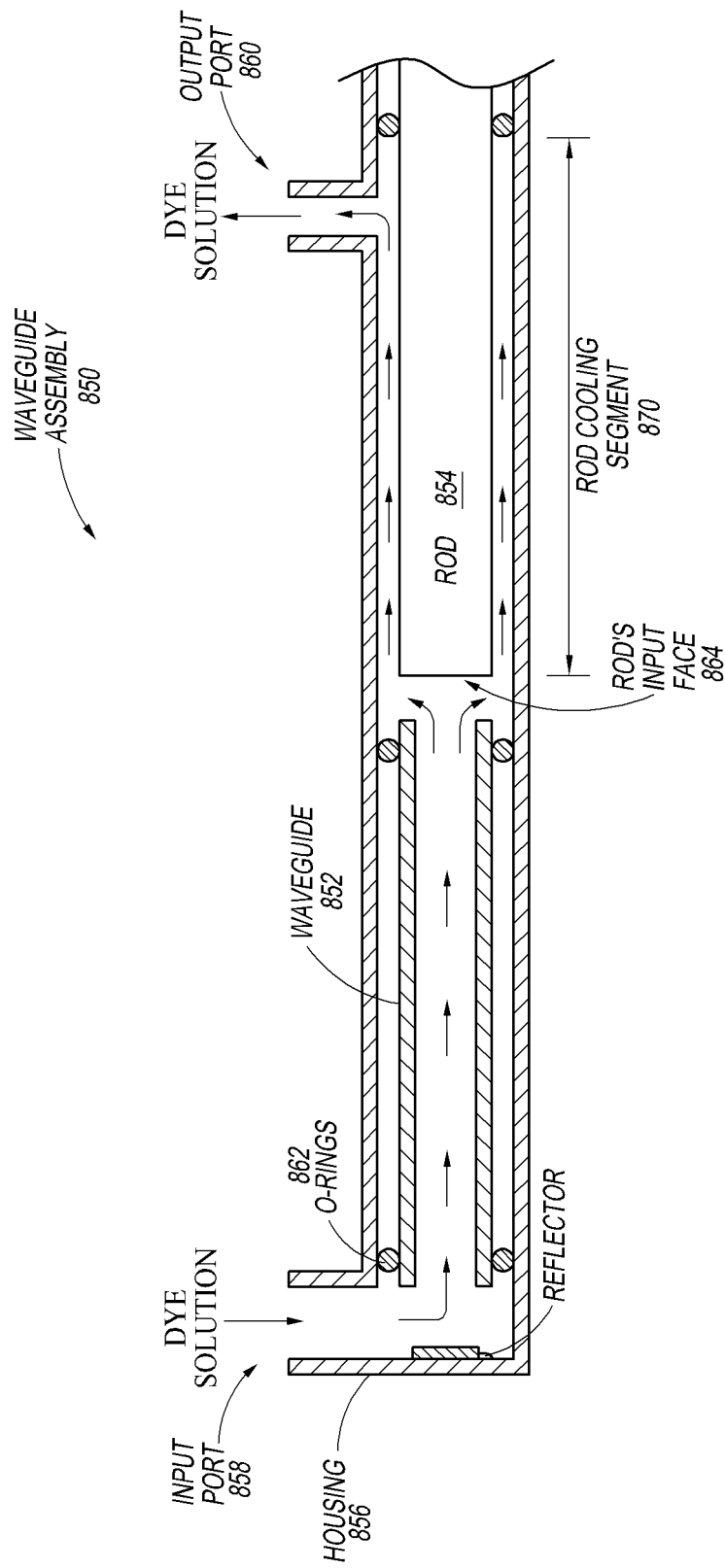
FIG. 11 illustrates another embodiment of the waveguide system of the handpiece of FIG. 9.

However, in the embodiment illustrated in FIG. 11, an alternate waveguide assembly 850 includes an output optic 854 positioned within a longer housing 856 to allow dye solution to flow around and cool a larger area of the rod 854. For example, the rod's input face 864 is proximally positioned with respect to the housing's output port 860 to create a rod cooling segment 870. In some embodiments, the rod cooling segment 870 is 40-50 mm long, and the entire rod length 854 is about 100 mm. The longer cooling segment 870 results in better contact cooling of the skin.

In addition, in some embodiments, the output optic is covered around its circumference with an optically-insulating coating, such as Teflon (PTFE AF-2400) or another material having a lower refractive index than the output optic. The Teflon coating has a refractive index that allows it to act as a cladding around the rod, which increases optical efficiency. In addition, the Teflon coating optically isolates the o-rings from the rod, which prevents optical leakage from the rod at the points where the rod would otherwise contact the o-rings. In some embodiments, the output optic is coated with a reflective material such as silver, gold, or an optical coating, i.e., having at least one layer of a dielectric material The same benefit may be obtained by using a waveguide having a high refractive index and cladding it with Teflon (or a similar insulator) around the areas in contact with the o-rings. In another embodiment, at least one of the o-ring areas of the waveguide is coated with a reflective material such as silver, gold, or an optical coating. In such an embodiment, the difference in indices of refraction between the o-rings and waveguide may not significantly affect the optical efficacy or protection of the o-rings. In some embodiments without a coating on the waveguide 110, the o-rings can be coated with PTFE or another low refractive index material to help minimize the loss of light leaking into the o-rings and to help protect the o-rings. The same or a similar o-ring arrangement can be used on the output optic 824 when the output optic 824 does not include a coating at the site of the o-rings.

In some alternative embodiments, the waveguide can be a substantially solid rod rather than a pipe having a passage for circulation or passing of a fluorescent substance. The waveguide can be, for example, a crystal or glass hosting an ion or ions. The solid waveguide can comprise, for example, fluorescent glass such as a Lumilass glass, e.g., Lumilass G9, available from Sumita, a solid state fluorescent medium, titanium-doped sapphire, a ruby (ruby crystal), erbium-doped YSGG, erbium-doped YAG, neodymium-doped YAG, chromium-doped crystal, or an Alexandrite (e.g., Alexandrite crystal). In some embodiments, the waveguide can comprise a polymer doped with a second fluorescent dye, which absorbs photonic energy from the source and transfers the energy to the fluorescent material, thereby increasing fluorescence efficiency of the system. In some embodiments, a solid fluorescent rod or at least one of a fluorescent gel contained by a solid body or a fluorescent liquid contained by a solid body (that can optionally be exchangeable or disposable) is provided. In some embodiments the solid fluorescent rod or at least one of a fluorescent gel contained by a solid body or a fluorescent liquid contained by a solid body can be construed from at least two sections along the axis of the waveguide. The handpiece can still only require a single reflector 170 opposite the handpiece output rather than two opposing mirrors as in a laser system. In some embodiments, a dye solution flows over and/or around the solid waveguide to cool the waveguide and to help produce extra energy to drive the rod.

In some embodiments, a flow jacket, e.g., a crystal, glass, or polymer tube can surround at least part of the waveguide. A gap between the waveguide and flow jacket can allow for the circulation of a temperature conditioning (e.g., cooling, heating, or stabilizing) liquid or gas over a portion of the waveguide. In some embodiments, the circulating liquid or gas can include at least one fluorescent material. The circulating liquid or gas can at least partially absorb light from the source and emit light at least partially absorbed by the fluorescent material in the waveguide or optional dopant in the waveguide. The circulating liquid or gas can also or alternatively emit light to be delivered to the biological tissue.

In some embodiments, the handpiece can include a selector capable of selecting for either light emitted from the waveguide or fluid circulating between the waveguide and flow jacket. In some embodiments, the selector selects for a fractional combination of light emitted by the waveguide and circulating fluid. The selector can be, for example, an optical filter, prism, coating, geometrical optical shape, or any other wavelength attenuating or wavelength selective optical component. The selector can be located anywhere along or surrounding the waveguide, output optic, skin contacting portion if present, or anywhere in between.

In some embodiments, the flow jacket can contain at least one fluorescent material. The flow jacket can absorb at least part of light emitted from the source and emit light that is delivered to the tissue and/or absorbed by the waveguide and/or the fluorescent circulating fluid. Light emitted by the fluorescent circulating fluid can in turn be delivered to tissue and/or absorbed by the waveguide. A selector can select for one of or a combination of light emitted by the flow jacket, waveguide, and/or circulating fluid.

Figure 12:
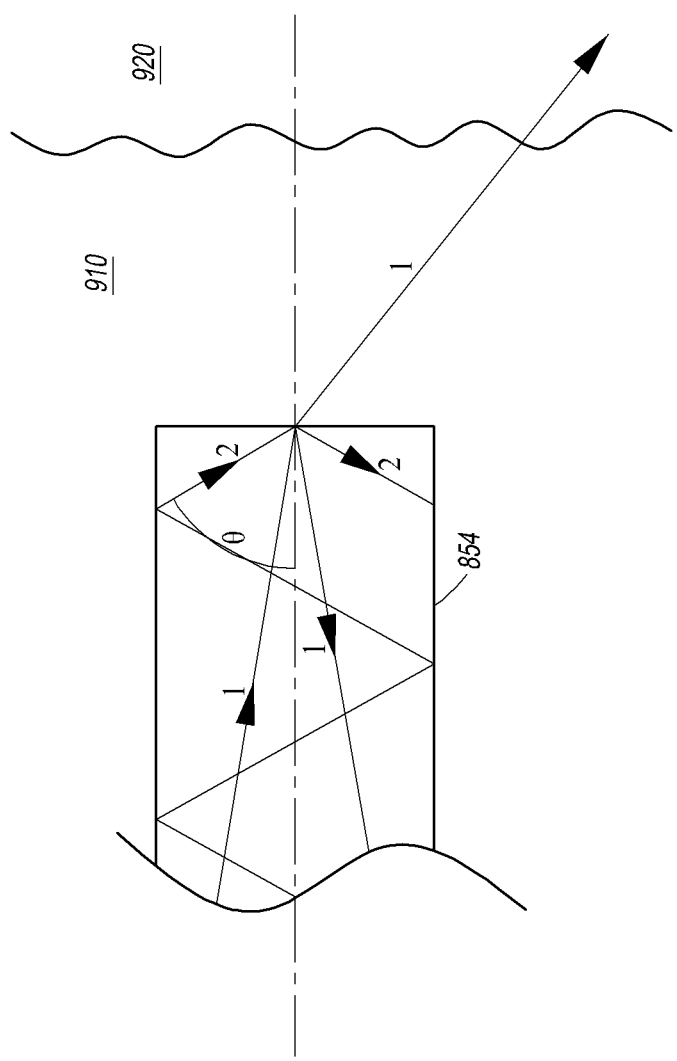
FIG. 12 illustrates an embodiment of a substantially cylindrical output optic.

As described herein, the waveguide 110 can be adapted to deliver electromagnetic radiation to skin 920 through a skin contacting portion 140 or output optic 854 adjacent the waveguide 110. The skin contacting portion 140 or output optic 854 can include, for example, a glass, silica, sapphire, or plastic. Direct contact with the skin 920 may be necessary due to scatter and total internal reflection that occurs at a boundary between the output optic 854, e.g., sapphire rod, and air when there is an air gap 910 between the output optic 854 and skin 920 as shown in FIG. 12. Different materials have different refractive indices. When light traveling through one material strikes a boundary with another material having a lower refractive index, the difference in refractive indices can cause a portion of the light to travel into the second material and a portion of the light to be reflected back into the first material. The difference in refractive indices can also cause refraction (change in the angle of propagation) of the light allowed into the second material. If the light strikes the boundary at an angle relative to normal that is greater than the critical angle (i.e., closer to being parallel to the boundary plane), all of the light is reflected back into the first material and none passes into the second.

When there is an air gap 910 between the output optic 854 and skin 920, the light must cross the output optic 854—air boundary and the air—skin 920 boundary. Because the output optic 854, e.g., sapphire, typically has a higher refractive index than air, a portion of light that impacts the output optic 854—air boundary at an angle of incidence less than the critical angle will be refracted and a portion will be reflected, as illustrated by ray 1 in FIG. 12. Light that impacts the boundary at an angle greater than the critical angle, e.g., angle $\theta$ in FIG. 12, will be totally reflected within the output optic 854 and none will cross the air gap 910, as illustrated by ray 2 in FIG. 12. Therefore, too much light can be lost when the light must travel first through air before reaching the skin. For example, in some cases about one-third of the total light reaches the skin 920.

Figure 13:
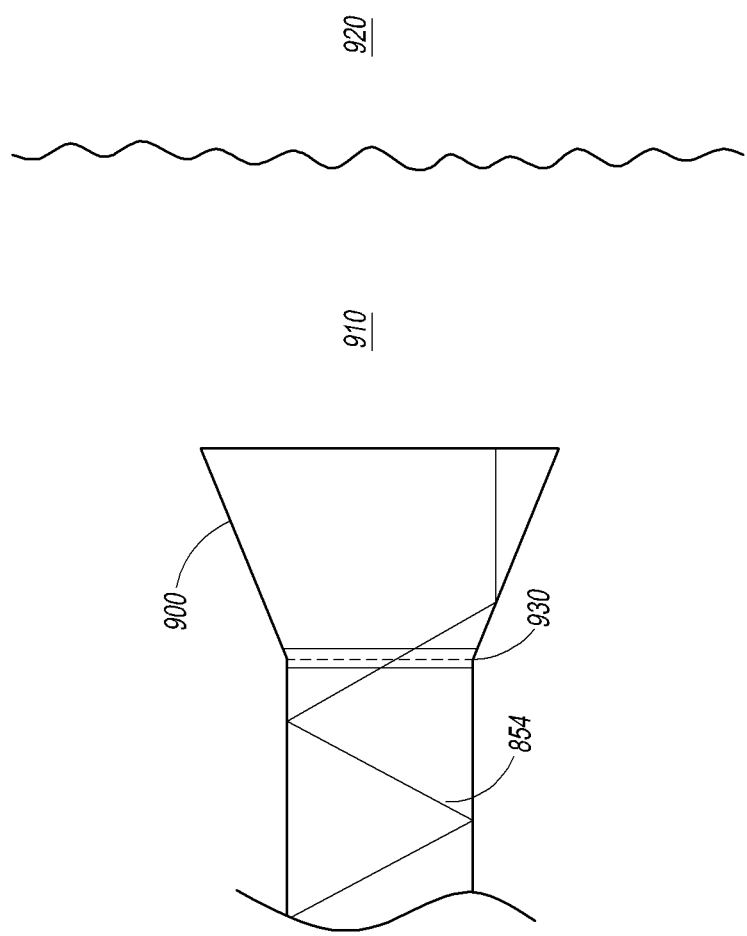
FIG. 13 illustrates an embodiment of the output optic of FIG. 12 having an optional flared end.

In some embodiments, however, the output optic 854 can be adapted to deliver electromagnetic radiation directly to the skin 920 without having to directly contact the skin 920, or to deliver electromagnetic radiation closer to perpendicular to the skin when in direct contact with the skin 920. The output optic 854 can include a flare 900, for example, as shown in FIG. 13, to form a lens system. The flare 900 can be, for example, a cylindrical flare or a truncated pyramid. The flare 900 can help change and control the angle of light traveling through the output optic 854 and reaching the boundary with air or a contact medium to help keep the angle of incidence less than the critical angle and reduce total internal reflection. In some embodiments, the flare 900 can increase the spot size from about 8 mm to about 16 mm. In some embodiments, the flare 900 can increase the spot size to, for example, about 10 mm, about 15 mm, about 20 mm, about 25 mm, about 30 mm, about 35 mm, about 40 mm, or 40×40 mm, or more. In some embodiments, the flare 900 can allow for about 95% of the light to reach the skin 920. The output optic 854 can be tapered or flared over its entire length, or only over a portion thereof, for example, as shown in FIG. 13. The flare can be ground, cast, machined or formed by any other appropriate method. In some embodiments, a tapered or flared tip can be removably attachable to the remainder of the output optic 954 via a coupling 930. A detachable tip can advantageously allow for easier sterilization between uses or can be disposable and replaceable between uses. Such a non-contact system can allow for an air gap 910 between the handpiece and skin 920 in use, which can advantageously allow the user to monitor the skin during treatment, for example, to ensure the treatment is working and/or to watch for adverse reactions. The non-contact system can also allow the user to avoid pressing blood out of the underlying vessels by compressing the skin 920. In some embodiments, an output optic to skin coupling substance can be applied to the skin 920 or end of the output optic 920 before or during treatment to, for example, enhance treatment light coupling to the tissue and/or inhibit adverse effects. For example, a gel, water, oil, silicone oil, fat, and/or petroleum jelly can be applied to the skin 920.

Figure 14A:
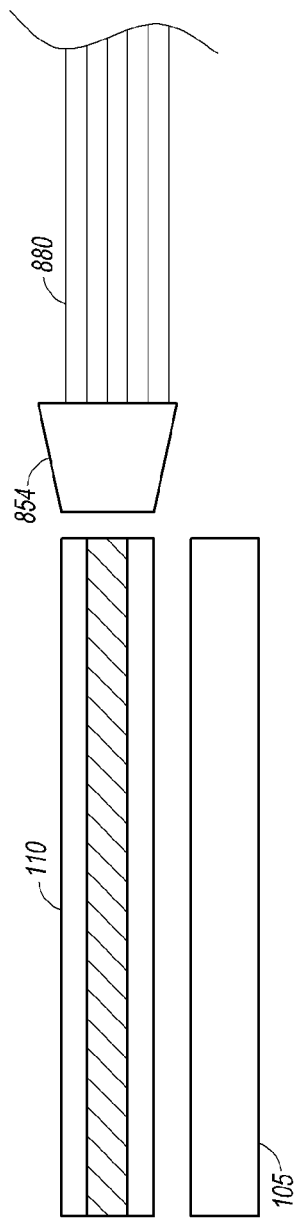
FIG. 14A illustrates a waveguide optically coupled to a fiber bundle with a flared output optic.

A flared output optic 854 can also be used to improve optical coupling to a fiber optic, or fiber bundle 880, for example as shown in FIG. 14A. The flared output optic 854 can also be used to improve optical coupling to a hollow waveguide, liquid waveguide, partially liquid waveguide, and/or another light guide. In some embodiments, it can be advantageous to locate the dye cell and/or any power, light, and/or fluid sources and/or conduits in a base unit, such as base unit 210, rather than transferring power, coolant, and/or a fluorescent substance or dye to the handpiece via, for example, the umbilicus 215. Locating these components of the apparatus 200 in the base unit 210 rather than the handpiece 100 can, for example, advantageously separate power and fluid sources and/or lines from the patient for safety and/or reduce the weight of the handpiece. A length of fiber bundle 880 or another output waveguide can be used to transfer just the output light from the base unit 210 to the handpiece 100. In some embodiments a fluorescent substance is located at least along the umbilicus. The flare output optic 854 can improve optical coupling to the fiber bundle 880 or other output waveguide so that enough light can be transferred to the patient for effective treatment.

Figure 14B:
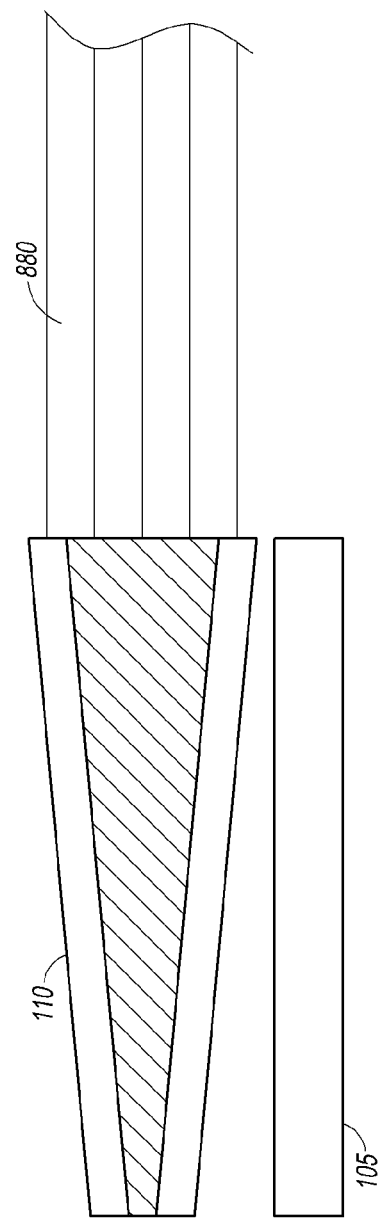
FIG. 14B illustrates a flared waveguide optically coupled directly to a fiber bundle.

If light strikes a boundary between the rod 854 and fiber bundle 880 at an angle relative to normal that is greater than the critical angle (i.e., closer to being parallel to the boundary plane), the light is transmitted through the fiber wall rather than being propagated along the length of the fiber bundle 880. In some embodiments, the critical angle is about 30°. The flared output optic 854 can be used to help change and control the angle of light traveling through the output optic 854 and reaching the boundary to keep the angle of incidence less than the critical angle and increase optical coupling into the fiber bundle. For example, if the refractive index of the flared portion of the output optic 854 is greater than that of a non-flared portion of the output optic 854, the dye cell, and/or another component in the light path prior to the flare, the light becomes more collimated. The tapered surface therefore changes the direction of light to decrease the cone angle and increase collimation of the output light. In some embodiments, the flared output optic 854 decreases the cone angle of the output light to about 30°. This advantageously promotes internal reflection within the fiber bundle 880. In some embodiments, the waveguide 110 or dye cell itself is flared, allowing the dye cell to be coupled directly to the fiber bundle 880 or other output waveguide without a separate output optic 854, for example as shown in FIG. 14B.

An example embodiment of an output optic 1824 that can be adapted to deliver electromagnetic radiation to skin 920 without having to directly contact the skin 920 is shown in FIGS. 15A and 15B. As shown, the output optic 1824 can include a rod 854, a hemispherical ball lens 1856, and an optical output waveguide 1858. The ball lens 1856 optically couples light from the rod 854 into the output waveguide 1858. The ball lens 1856 advantageously mitigates the total internal reflection that can result at a flat output surface. In some embodiments, other negative lenses can be used to mitigate total internal reflection. In some embodiments, a diameter of the ball lens 1856 is larger than a diameter of the rod 854. In some embodiments, the rod 854 is not required, and the ball lens 854 can couple light directly from the waveguide or dye cell 110 to the output waveguide 1858.

The output waveguide 1858 can have non-curved edges. The output waveguide 1858 can be shaped as, for example, a compound parabolic concentrator, a straight horn, or a parabolic horn. In some embodiments, the output waveguide 1858 can have a truncated pyramid shape, for example, a square truncated pyramid shape. In some embodiments, the output waveguide 1858 is hollow, and the ball lens 1856 can be housed within the output waveguide 1858 with the flat side of the ball lens 1856 and the top or small end of the output waveguide 1858 aligned with one another and facing the rod 854. In some embodiments, the output optic 1824 need not include the ball lens 1856, and the output waveguide 1858 can be solid or partially solid. The output waveguide 1858 can be made of, for example, PMMA, glass, crystal, PTFE, a liquid, and/or a semiliquid such as, for example, a gel, oil, or polymer.

The bottom or large end of the output waveguide 1858 is directed to the skin 920 to be treated in use. The bottom of the output waveguide 1858 can, but need not, be placed in contact with the skin 920 during use. The ball lens 1856 can disperse the output light from the rod 854 or waveguide 110 to create a larger treatment spot size, which can increase the speed and/or efficiency of the treatment. The output waveguide 1858 helps direct the output light to produce a treatment spot on the skin 920 having non-curved edges, for example, a square-shaped treatment spot. The straight edges of the treatment spot can advantageously allow for a grid treatment pattern when treating large areas. This allows the physician to cover the entire area to be treated without gaps or overlap between adjacent spots.

In some embodiments, a diameter of the ball lens 1856 can be substantially equal to and slightly smaller than a length and width of the top of the output waveguide 1858 so that the ball lens 1856 contacts or nearly contacts an inner surface of the top of the output waveguide 1858 at a middle portion of each side of the top of the output waveguide 1858, as shown in FIG. 15B. The placement of the ball lens 1856 within the output waveguide 1858 and shapes of the ball lens 1856 and output waveguide 1858 provide for gaps 1859 between the ball lens 1856 and corners of the top of the output waveguide 1858. In some embodiments, air is flowed into the output waveguide 1858 through the gaps 1859, which can advantageously help cool the output waveguide 1858 and/or the skin 920 during use. The waveguide assembly can include flow paths 1860 for air, another gas, and/or a liquid spray running alongside the waveguide 110 from a source to the gaps 1859. In some embodiments including a non-hollow or partially non-hollow output waveguide 1858, air or other flow channels can be formed or disposed in the output waveguide 1858 to provide cooling. In some embodiments, air, gas, and/or liquid can be delivered to the skin outside of the output waveguide 1858.

As discussed above, in some embodiments air cooling and/or liquid spray cooling can provide additional advantages when the output waveguide is placed in direct or indirect contact (e.g., contact via a gel or other intermediary substance) with the patient's tissue (e.g., skin). In some embodiments, spray, mist, air, etc. is emitted from the side of the waveguide (e.g., the output waveguide 1858). In other embodiments, the spray, mist, air, etc. is delivered through at least a portion of a partially hollow or perforated waveguide to the patient's tissue. Indeed, in such embodiments, the spray, etc., and light may be transmitted through the same lumen of the handpiece to the patient's tissue. For example, the spray and light may be transmitted through an output waveguide, such as the output waveguide 1858 described above, or any other output waveguide. Such waveguides include any of the waveguides described herein, including a tapered, straight, and/or flared quadratic horn having a reflective inner surface, a tube having a reflective inner surface, a fiber optic having a lumen to carry spray, air, water, etc.

In some embodiments, the devices and methods described herein can be used for hair removal. Irradiating at least part of the skin, hair, or hair follicle can be used for temporary, long term, and in some cases, permanent removal of hair. Pigmentation, such as melanin, in the hair (including the hair cortex and in some cases, the surrounding tissue), acts as a chromophore that absorbs light by selective photothermolysis. Blood can also act as a chromophore when light is directed at certain tissues, e.g., at the bulb of the hair follicle.

Light having wavelengths above at least 500 nm may be used to remove such pigment-containing hair. Typical wavelengths used to do so generally have long path bandwidths of substantially 600 nm or more, in order to avoid side effects resulting from light absorption by blood. For example, light having a wavelength of 600 nm or more, 615 nm or more, 650 nm or more and sometimes 680 nm or more, has been used. Such light may be produced from a variety of light sources, including a Xenon flashlamp, a Krypton flashlamp, or a Xenon-Krypton flashlamp. Other suitable light sources are Nd:YAG lasers at 1064 nm, KTP crystal, frequency doubled Nd:YAG lasers at 532 nm, dye lasers and TRASERs above 600 nm, ruby lasers at 694 nm, Alexandrite lasers at 755 nm and diode lasers at, for example, 810 nm. In some embodiments, a TRASER is any of the fluorescent light generating devices described above.

However, while the above-described techniques are often effective for darker hair, for example, brown and black hair, these techniques are typically not effective for temporary, long-term, or permanent removal of lighter hair, for example, blond, gray, or white hair. Such techniques are generally unsuccessful at removing these low-pigment hair types because they lack a chromophore that can be used effectively with such light sources. Therefore, previously known methods and devices based on electromagnetic radiation have not been able to be used for temporary, long term, or permanent removal of light hair, for example, blond, gray, or white hair. Keratin, which is found in hair, can also act as a chromophore and can absorb light having a wavelength of about 3,000 nm+/−300 nm. However, in some cases, use of such wavelengths or light sources emitting these wavelengths are not preferred because water exhibits high absorption of such wavelengths and such light sources are typically expensive and low power.

Surprisingly, experiments have shown that directing blue and/or blue-green light at, and causing absorption of the blue and/or blue-green light by, one or more of on the hair shaft, in the hair shaft, in any of the root sheaths, and/or in the space between the hair surface and the inner root sheet can effectively remove low-pigment hair types (e.g., blond, gray or white-colored hair, etc.). Such blue and/or blue-green light can have a wavelength of about 380 nm, about 530 nm, in the range of about 380 nm to about 530 nm, or in the range of about 400 nm to about 500 nm.

Blood also exhibits at least some absorption of wavelengths in these ranges, which can cause adverse effects. Significant light absorption by blood and potential resulting side effects can be mitigated by avoiding the use of light having a wavelength in the range of, e.g., about 380 nm to 460 nm, about 400 nm to 450 nm, or about 410 nm to 440 nm. In other words, light absorption competition with blood can be reduced by avoiding using at least some light where blood has absorption or strong absorption. Water, which can be found in, for example, the tissue surrounding hair and the hair follicle, generally has weak absorption and is not a significant competitor to absorption in the spectral area of about 380 nm to about 530 nm, or about 400 nm to 500 nm.

These wavelengths, for example, in the range of about 380 nm to 460 nm, about 400 nm to 450 nm, or about 410 nm to 440 nm, can be selected to target previously unknown chromophores at a part, substructure, or structure of a hair shaft, hair follicle, sebum or sebaceous gland. In some embodiments, the wavelengths are selected to target one or more sebum, fatty acid(s), phytoshingosine, ceramide, cholesterol, cholesterol sulfate, and/or cholesterol oleate. In some embodiments, the light is selected to target a fatty layer of the hair, on an outer surface of the hair, in the hair, and/or between keratin flakes of the hair. The resulting hair removal can be temporary, long term, or permanent. In some embodiments, wavelengths in the range of about 430-500 nm, about 440-500 nm, or about 450-500 nm can be used to target such chromophores.

In some embodiments, devices as described herein can be configured to direct light having a wavelength between about 380 nm and 530 nm light to a chromophore, such as lipids, located in the hair shaft (including under the skin surface), on the hair shaft (including under the skin surface), in the hair follicle, and/or in the sebaceous gland. Absorption of the light by the chromophore heats up at least one of the structures of the hair shaft, the hair follicle, or the sebaceous gland, in order to achieve at least one of temporary, long term, and permanent removal of low pigment hair (e.g., white, gray, or blond hair). In some embodiments, heat is conducted to hair-building stem cells in at least one of the hair follicle's bulge or bulb. In some embodiments, the hair-building stem cells are damaged or killed by the heat.

The devices can generate continuous or pulsed light. The devices can be used to irradiate one or more hairs and/or one or more hair follicles. The light source can include any one or more of a LASER (light amplification by stimulated emission of radiation), intense pulsed light source (IPL), a fluorescent pulsed light source (FPL), a TRASER (total internal amplification of spontaneous emission of radiation), and a light emitting diode (LED). The energy density of such devices (e.g., fluence) can be, for example, within the range of about 1 J/cm$^2$ to 100 J/cm$^2$. The light pulse width or pulse train length can be, for example, within the range of about 0.5 ms to 20 minutes, or 0.5 ms to 60 minutes.

In some embodiments, a method of removing low-pigmentation hair can include moving the light exposure in a manner such that it repeatedly irradiates an area before it has thermally relaxed. In some embodiments, the devices and methods can include systems and methods for cooling of the skin. This can be accomplished by, for example, contact cooling with or without an optical or thermal contacting media, spray cooling, and/or air flow cooling. The cooling can be applied before, during, and/or after the light exposure. The cooling can be applied to a predetermined depth.

Figure 16:
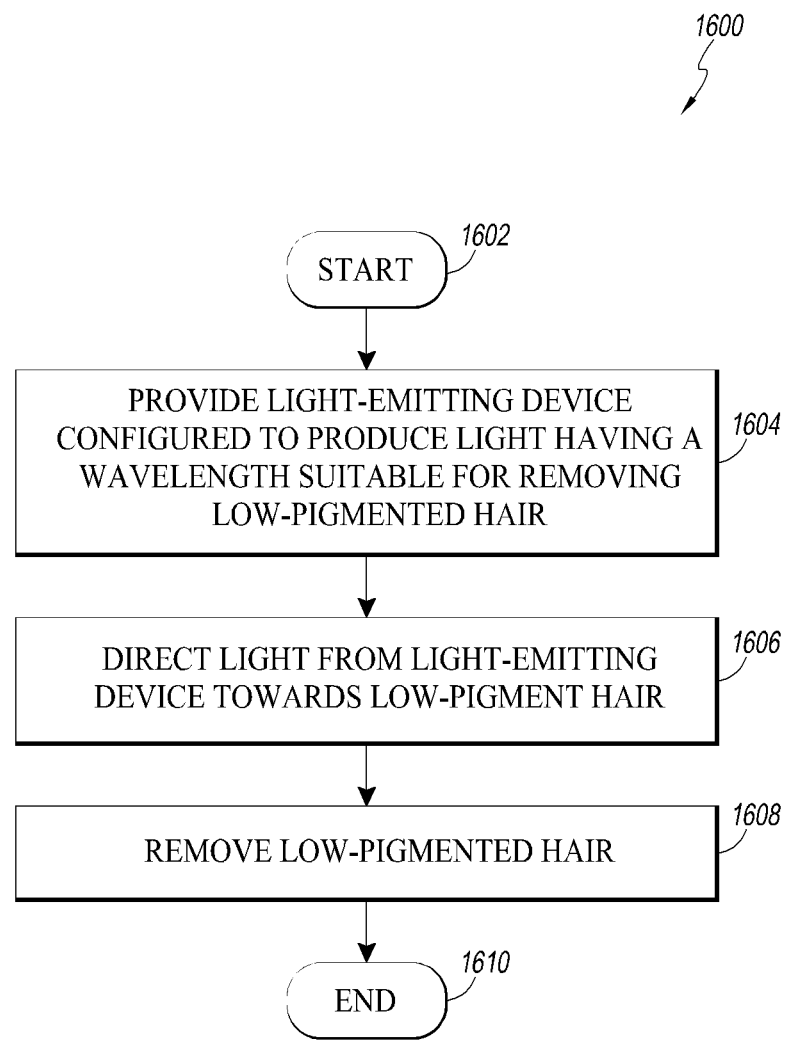
FIG. 16 is a flowchart illustrating a method of low-pigmented hair removal.

One embodiment of a method of removing low-pigment hair using any of the devices and techniques described above (including a TRASER, e.g., a fluorescent handpiece) is illustrated in FIG. 16. The method 1600 begins at block 1602. At block 1604, a light-emitting device configured to product light having a wavelength suitable for removing low-pigmented hair is provided. Such devices and wavelengths include any of the devices and wavelengths described above. At block 1606, light is directed from the light-emitting device toward low-pigment hair. For example the light may be directed to any portion of low-pigmented hair described above, including a hair follicle, a hair shaft sebaceous gland, or any other portion of the hair, including any chromophore described above. At block 1608, hair is removed once sufficient light is directed to the hair. The method 1600 ends at block 1610.

While the invention has been particularly shown and described with reference to specific embodiments, it should be understood by those skilled in the art that various changes in form and detail may be made without departing from the spirit and scope of the invention as defined by the appended claims. For example, various components as described herein can be combined and used in various combinations and subcombinations.

APPENDIX A

Dyes, solvents and additives that may be used in combination to form dye solutions in accordance with various embodiments include, but are not limited to:

Water soluble dyes which may be used alone or in combination include but are not limited to:

| Dye | Solubility grams/liter | labs[1] (nm) | lfl (nm) |
|---|---|---|---|
| IR 125 | 1.4-3$^w$, soluble$^m$ | 678$^w$, 800$^{w/LO}$, 795$^s$ | 833$^s$ |
| HITC Special | 2.1$^w$, soluble$^m$ | 741$^w$, 757$^{w/LO}$ | ~743$^e$, 751$^s$ |
| Oxazine 750 Chloride | ~2.3$^w$, ~50$^m$ | 662$^m$ | 678$^m$ |
| Oxazine 725 Chloride | ~3.1$^w$, soluble$^m$ | 645$^e$ | 680$^e$ |
| Oxazine 720 Chloride | ~17$^w$, soluble$^m$ | 627$^e$ | 650$^e$ |
| Sulforhodamine 640 | ~1$^w$, 34$^m$ | 576$^e$, 586$^{w\ or\ w/LO\ 1}$ | 602$^e$ |
| Kiton Red 620 | 92$^w$, 158$^m$ | 554$^e$, 566$^{w\ or\ w/LO}$ | 575$^e$ |
| Rhodamine 590 Chloride | 4.8$^w$, 665$^m$ | 530$^e$ | 560$^e$ |
| Pyrromethene 556 | 6$^w$, 0.74$^m$ | 492$^m$, 490.6$^w$ | 533$^m$ |
| Disodium Fluorescein | soluble$^{w,m}$ | 501$^e$ | 531$^e$ |
| Silbene 420 | 34$^w$, 14$^m$ | 349$^m$ | 425$^{e(402,450sh)}$ |

General fluorescent dyes which may be used alone or in combination include but are not limited to:

| Laser Dye |
|---|
| DMQ |
| QUI |
| TBS |
| DMT |
| p-Terphenyl |
| TMQ |
| BPBD-365 |
| PBD |
| PPO |
| p-Quaterphenyl |
| Exalite 377E |
| Exalite 392E |
| Exalite 400E |
| Exalite 348 |
| Exalite 351 |
| Exalite 360 |
| Exalite 376 |
| Exalite 384 |
| Exalite 389 |
| Exalite 392A |
| Exalite 398 |
| Exalite 404 |
| Exalite 411 |
| Exalite 416 |
| Exalite 417 |
| Exalite 428 |
| BBO |
| LD 390 |
| a-NPO |
| PBBO |
| DPS |
| BBO |
| POPOP |
| Bis-MSB |
| Stilbene 420 |
| LD 423 |
| LD 425 |
| Carbostyryl 165 |
| Coumarin 440 |
| Coumarin 445 |
| Coumarin 450 |
| Coumarin 456 |
| Coumarin 460 |
| Coumarin 461 |
| LD 466 |
| LD 473 |
| Coumarin 478 |
| Coumarin 480 |
| Coumarin 481 |
| Coumarin 485 |
| Coumarin 487 |
| LD 489 |

| Laser Dye |
| --- |
| Coumarin 490 |
| LD 490 |
| Coumarin 498 |
| Coumarin 500 |
| Coumarin 503 |
| Coumarin 504 (Coumarin 314) |
| Coumarin 504T (Coumarin 314T) |
| Coumarin 510 |
| Coumarin 515 |
| Coumarin 519 |
| Coumarin 521 |
| Coumarin 521T |
| Coumarin 522B |
| Coumarin 523 |
| Coumarin 525 |
| Coumarin 535 |
| Coumarin 540 |
| Coumarin 540A |
| Coumarin 545 |
| Pyrromethene 546 |
| Pyrromethene 556 |
| Pyrromethene 567 |
| Pyrromethene 567A |
| Pyrromethene 580 |
| Pyrromethene 597 |
| Pyrromethene 597-8C9 |
| Pyrromethene 605 |
| Pyrromethene 650 |
| Fluorescein 548 |
| Disodium Fluorescein |
| Fluorol 555 |
| Rhodamine 3B Perchlorate |
| Rhodamine 560 Chloride |
| Rhodamine 560 Perchlorate |
| Rhodamine 575 |
| Rhodamine 19 Perchlorate |
| Rhodamine 590 Chloride |
| Rhodamine 590 Tetrafluoroborate |
| Rhodamine 590 Perchlorate |
| Rhodamine 610 Chloride |
| Rhodamine 610 Tetrafluoroborate |
| Rhodamine 610 Perchlorate |
| Kiton Red 620 |
| Rhodamine 640 Perchlorate |
| Sulforhodamine 640 |
| DODC Iodide |
| DCM |
| DCM Special |
| LD 688 |
| LDS 698 |
| LDS 720 |
| LDS 722 |
| LDS 730 |
| LDS 750 |
| LDS 751 |
| LDS 759 |
| LDS 765 |
| LDS 798 |
| LDS 821 |
| LDS 867 |
| Styryl 15 |
| LDS 925 |
| LDS 950 |
| Phenoxazone 660 |
| Cresyl Violet 670 Perchlorate |
| Nile Blue 690 Perchlorate |
| LD 690 Perchlorate |
| LD 700 Perchlorate |
| Oxazine 720 Perchlorate |
| Oxazine 725 Perchlorate |
| HIDC Iodide |
| Oxazine 750 Perchlorate |
| LD 800 |
| DOTC Iodide |
| DOTC Perchlorate |
| HITC Perchlorate |
| HITC Iodide |
| DTTC Iodide |
| IR 144 |
| IR 125 |
| IR 143 |
| IR 140 |
| IR 26 |
| DMOTC |

Solvents which may be used alone or in combination include but are not limited to: Water, ethanol, methanol, glycol, glycerol, ethylene glycol, propylene glycol, propylene carbonate, acetone (low polar solvent), DMSO, benzene, benzyl alcohol, toluene, diesel, 9-Methylanthracene (non polar solvent), dimethylsulfoxide.

Additives which may be used alone or in combination include but are not limited to: COT cyclo-octo-tetraene (tripplet quencher), Amonyx LO (detergent), azeotropic amounts of a second solvent, saturable absorbers, fluorescent dye modelocking saturable absorbers.

Saturable absorbers which may be used alone or in combination include but are not limited to:

| Saturable Absorber |
| --- |
| BDN |
| Cryptocyanine |
| DASBTI |
| DASPI |
| DCI' |
| DDBCI |
| DDI |
| DI |
| DMETCI |
| DNTTCI |
| DOCI |
| DODCI |
| DOTCI |
| DQOCI |
| DQTCI |
| DQTCI' |
| DQTrCI |
| DTCI |
| DTDCI |
| DTP |
| HDITCP |
| HICI |
| HIDCI |
| HITCI |
| IR-140 |

| Saturable Absorber |
| --- |
| IR-143 |
| Malachite Green |
| NCI |
| PICI |
| Pinacyanol |
| Q-Switch I |
| Q-Switch 5 |
| Saturable Absorber 580 |

Fluorescent dye modelocking saturable absorbers which may be used alone or in combination include but are not limited to:

DASPI 04620
DASBTI 05360
DOCI 05410
DMETCI 05240
PICI 05200
DQOCI 05920
Pinacyanol 05940
DODCI 06480
Green 06480 + 20100
Saturable Absorber 580 05800
Cresyl Violet 06700
DQTCI 06220
DCI' 05950
DOTCI 08250
DOTCI + DCI 08250 + 07070
Cryptocyanine 07070
DQTCI 06220
DQTCI' 06240
DTDCI 07310
Cryptocyanine 07070
DDI 08100
DOTCI 08250
IR-140 09500
DI 05235
DDI 08100
HITCI 08422
NCI 07730
DASPI 04620
DASBTI 05360
DOCI 05410
DMETCI 05240
PICI 05200
DQOCI 05920
Pinacyanol 05940
DOCI 05410
HICI 05670
DASBTI 05360
DQOCI 05920
DQOCI + DODCI 05920 + 06480
DODCI 06480
DODCI + Malachite
DODCI 06480
DQTCI 06220
DQTCI' 06240
DTDCI 07310
Cryptocyanine 07070
DDI 08100
DOTCI 08250
IR-140 09500

What is claimed is:

1. A light-emitting, therapeutic system configured to treat biological tissue, comprising:
   a source of electromagnetic radiation;
   a waveguide positioned to receive electromagnetic radiation from the source, the waveguide comprising:
      first and second ends, and a wall extending therebetween, the wall configured to at least partially transmit the electromagnetic radiation therethrough, the wall defining a passage extending along a direction between said first and second ends;
      a fluorescent substance flowable within the passage, the fluorescent substance comprising a liquid base and a fluorescing agent; and
      a first port and a second port in fluid communication with the passage;
   an optical output element near one of the first and second ends of the waveguide;
   wherein the fluorescent substance is configured to absorb at least a portion of the electromagnetic radiation from the source through the wall and generate fluorescent light in response to the electromagnetic radiation, wherein the waveguide is configured to guide the fluorescent light emitted by the fluorescent substance towards the optical output element by internally reflecting at least a portion of the fluorescent light, and wherein the optical output element is configured to direct at least a portion of the fluorescent light towards biological tissue;
   a fluid conduit in fluid communication with the first and second ports and configured to carry the fluorescent substance between the waveguide's passage and a fluid moving system, the fluid moving system adapted to move the fluorescent substance from the first end to the second end through the passage and from the second end back to the first end through the fluid conduit; and
   a polarity filter configured to be coupled to the fluid conduit and to remove the fluorescing agent from the fluorescent substance, the fluid conduit being configured to direct the fluorescent substance through the polarity filter during a first mode of operation and to bypass the polarity filter during a second mode of operation.

* * * * *